United States Patent
Enger et al.

(10) Patent No.: US 12,318,629 B2
(45) Date of Patent: Jun. 3, 2025

(54) RADIATION SHIELDS FOR BRACHYTHERAPY

(71) Applicant: THE ROYAL INSTITUTION FOR THE ADVANCEMENT OF LEARNING / MCGILL UNIVERSITY, Montréal (CA)

(72) Inventors: Shirin Abbasi Enger, Montreal (CA); Marc Morcos, Baltimore, MD (US); Gabriel Famulari, Montreal (CA); Tristan Shoemaker, Acton, MA (US)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 497 days.

(21) Appl. No.: 17/617,529

(22) PCT Filed: Jun. 12, 2020

(86) PCT No.: PCT/CA2020/050821
§ 371 (c)(1),
(2) Date: Dec. 8, 2021

(87) PCT Pub. No.: WO2020/248073
PCT Pub. Date: Dec. 17, 2020

(65) Prior Publication Data
US 2022/0233882 A1    Jul. 28, 2022

Related U.S. Application Data

(60) Provisional application No. 62/861,052, filed on Jun. 13, 2019.

(51) Int. Cl.
    *A61N 5/10*    (2006.01)

(52) U.S. Cl.
    CPC .......... *A61N 5/1014* (2013.01); *A61N 5/1016* (2013.01); *A61N 2005/1024* (2013.01); *A61N 2005/1094* (2013.01)

(58) Field of Classification Search
    CPC ...... A61N 5/11; A61N 5/1001; A61N 5/1002; A61N 5/1014; A61N 5/1027;
    (Continued)

(56) References Cited

U.S. PATENT DOCUMENTS

| 5,302,168 A * | 4/1994 | Hess ............... A61N 5/1002 606/7 |
| 6,183,410 B1 * | 2/2001 | Jacobsen .......... A61N 5/1002 600/3 |

(Continued)

FOREIGN PATENT DOCUMENTS

| AT | 407 009 | 11/2000 |
| EP | 1060764 | 12/2000 |
| WO | 2018148464 | 8/2018 |

OTHER PUBLICATIONS

Dadkhah Hossein et al: "Multisource Rotating Shield Brachytherapy Apparatus for Prostate Cancer", International Journal of Radiation: Oncology Biology Physics, Pergamon Press, USA, vol. 99, No. 3, Jun. 20, 2017 (Jun. 20, 2017), pp. 719-728, XP085180558.
(Continued)

*Primary Examiner* — Samuel G Gilbert
(74) *Attorney, Agent, or Firm* — Norton Rose Fulbright Canada

(57) ABSTRACT

A shield assembly for an intensity modulated brachytherapy (IMBT) system, has: a tubular applicator engageable to a rotating mechanism of the IMBT system, the tubular applicator having a peripheral wall enclosing an internal cavity extending longitudinally along a central axis; a radiation shield extending axially along the central axis and received within the internal cavity, the radiation shield made of an (Continued)

MRI-compatible and radiation attenuating material; and a radionuclide-receiving passage within the internal cavity of the tubular applicator, the radionuclide-receiving passage extending axially and being radially offset from the central axis.

18 Claims, 14 Drawing Sheets

(58) Field of Classification Search
CPC .... A61N 2005/1094; A61N 2005/1005; A61N 2005/1018
See application file for complete search history.

(56) References Cited

U.S. PATENT DOCUMENTS

| | | | |
|---|---|---|---|
| 6,238,332 B1* | 5/2001 | Kanesaka | A61N 5/1002 600/3 |
| 6,264,599 B1 | 7/2001 | Slater et al. | |
| 7,232,408 B1* | 6/2007 | Fritz | A61N 5/1002 600/3 |
| 10,029,118 B2 | 7/2018 | Flynn et al. | |
| 2006/0116546 A1 | 6/2006 | Eng | |
| 2011/0270395 A1* | 11/2011 | Blackwell | A61F 2/4465 600/3 |
| 2013/0060239 A1 | 3/2013 | Hinman et al. | |
| 2015/0367144 A1 | 12/2015 | Flynn et al. | |
| 2017/0165500 A1* | 6/2017 | Flynn | A61N 5/103 |
| 2018/0277272 A1* | 9/2018 | Park | G21F 3/00 |
| 2019/0329066 A1* | 10/2019 | Lim | A61N 5/1007 |

OTHER PUBLICATIONS

Callaghan Cameron Met Al: "Systematic Review of Intensity-Modulated Brachytherapy (IMBT): Static and Dynamic Techniques", International Journal of Radiation: Oncology Biology Physics, Pergamon Press, USA, vol. 105, No. 1, Apr. 23, 2019 (Apr. 23, 2019), pp. 206-221, XP085784050.

Webster Matthew Jet Al: "Hdr brachytherapy of rectal cancer using a novel grooved-shielding applicator design", Medical Physics, AIP, Melville, NY, US, vol. 40, No. 9, Sep. 1, 2013 (Sep. 1, 2013), XP012178361.

European Search Report issued on Sep. 21, 2023 for corresponding application 20822983.

Adams, Quentin E et al., Interstitial rotating shield brachytherapy for prostate cancer, Medical physics vol. 41, No. 5, May 2014, 051703.

* cited by examiner

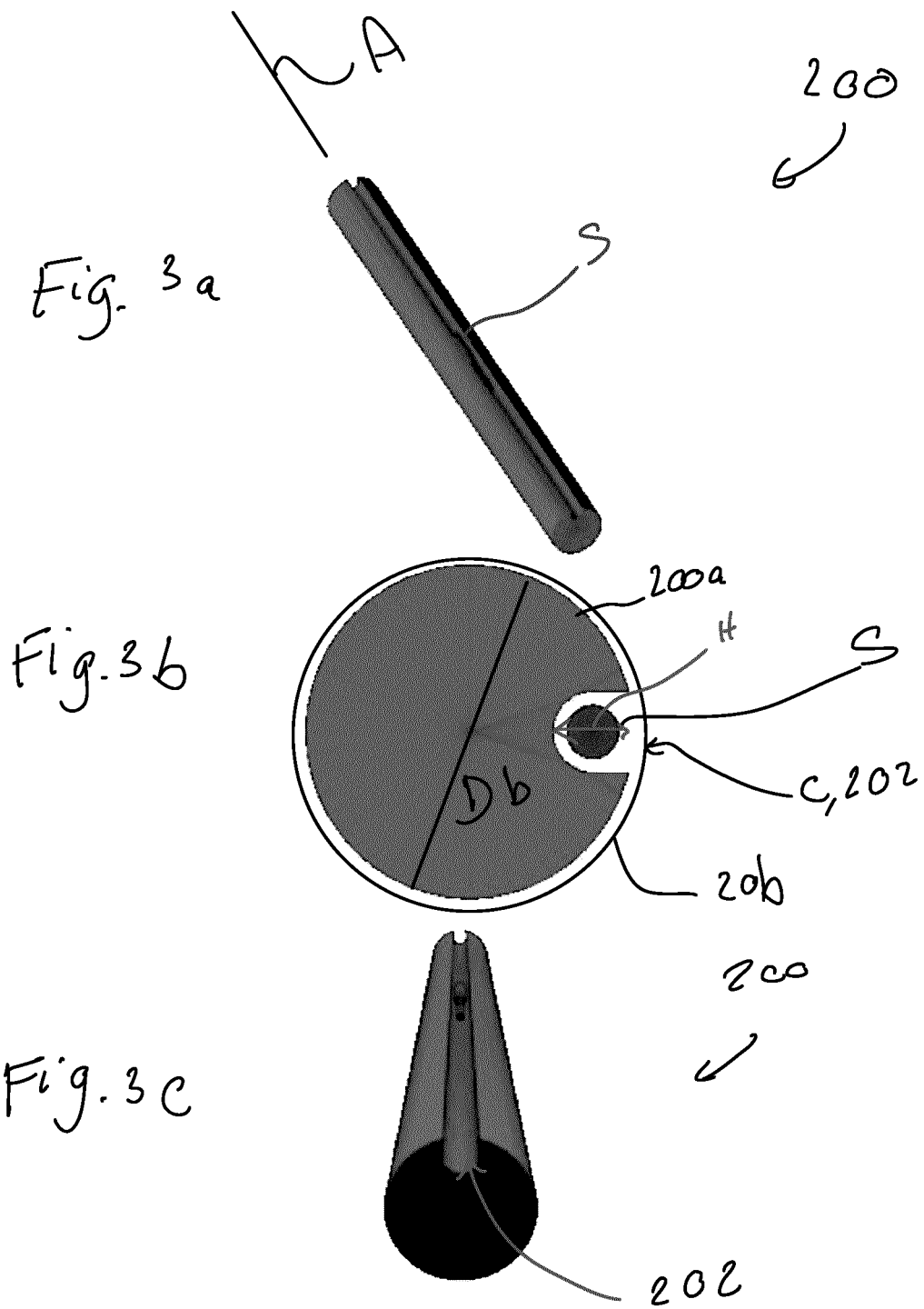

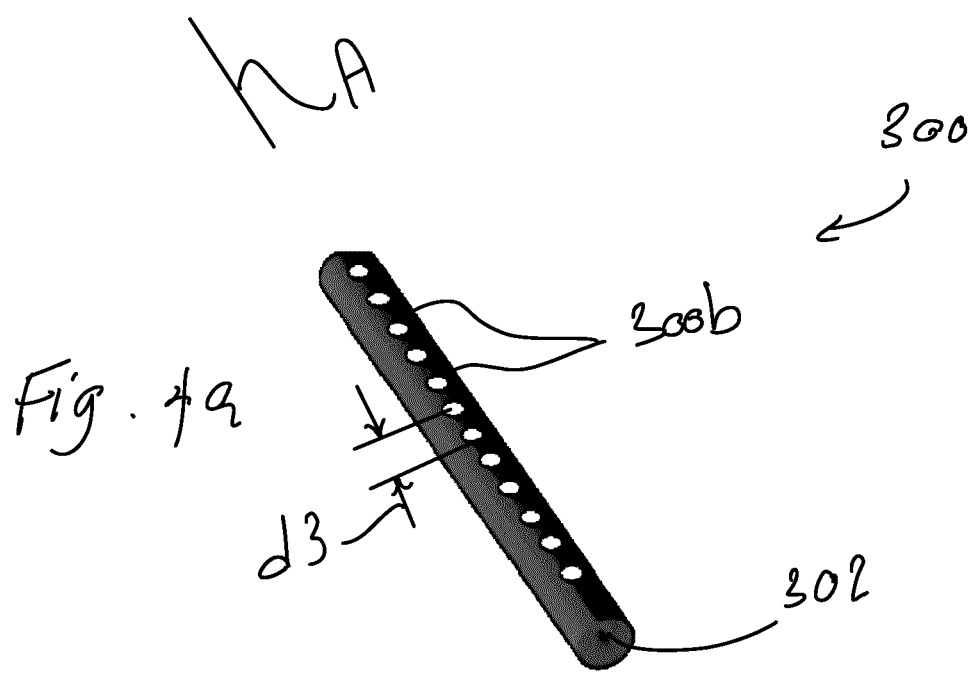
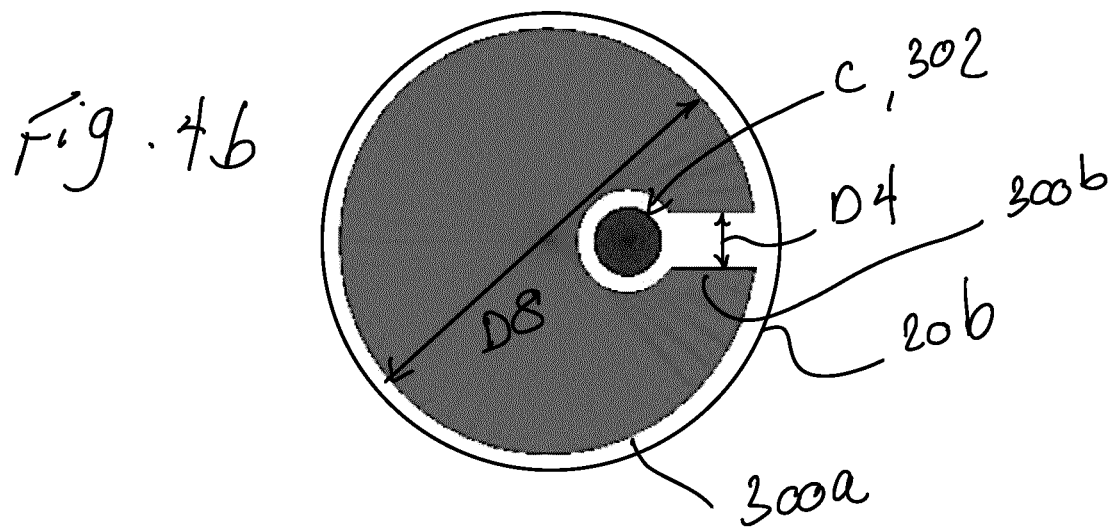
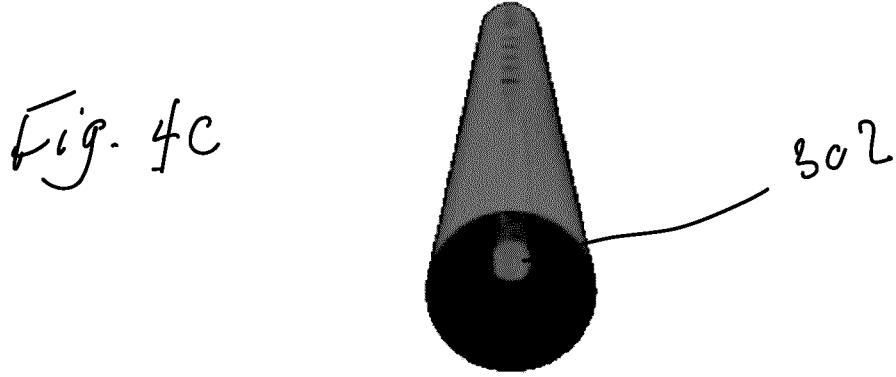

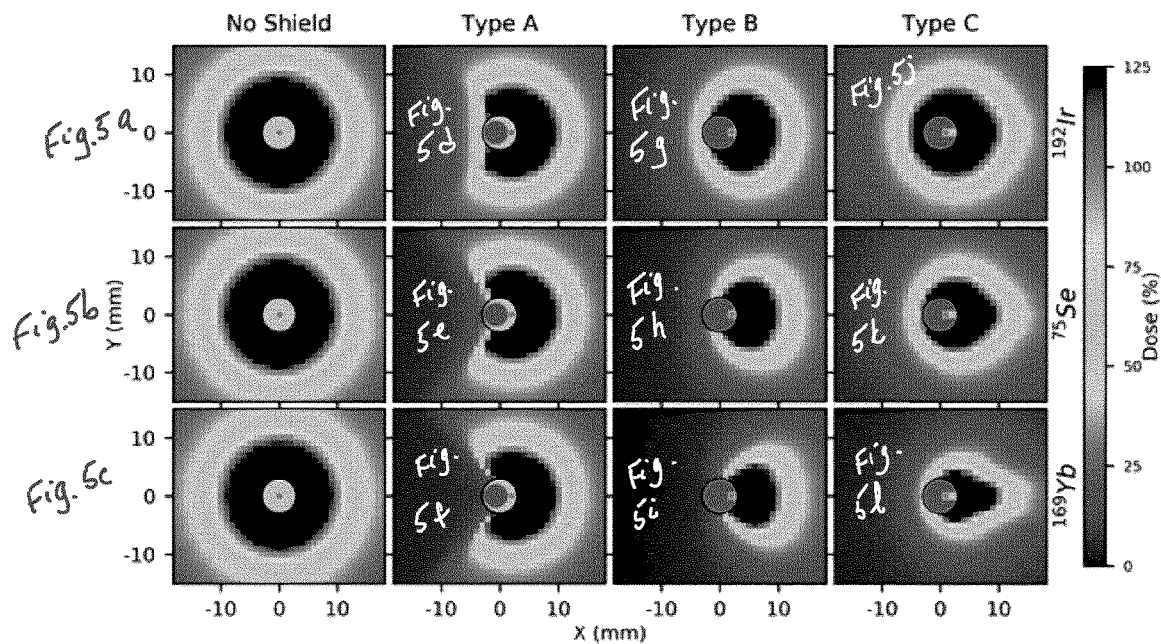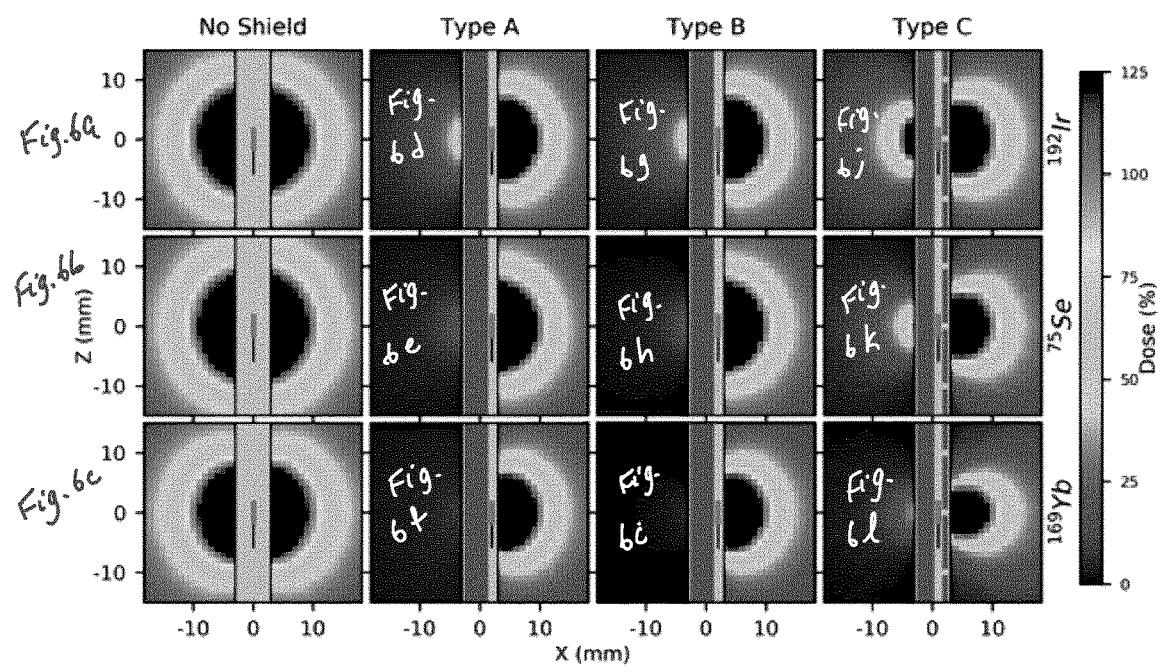

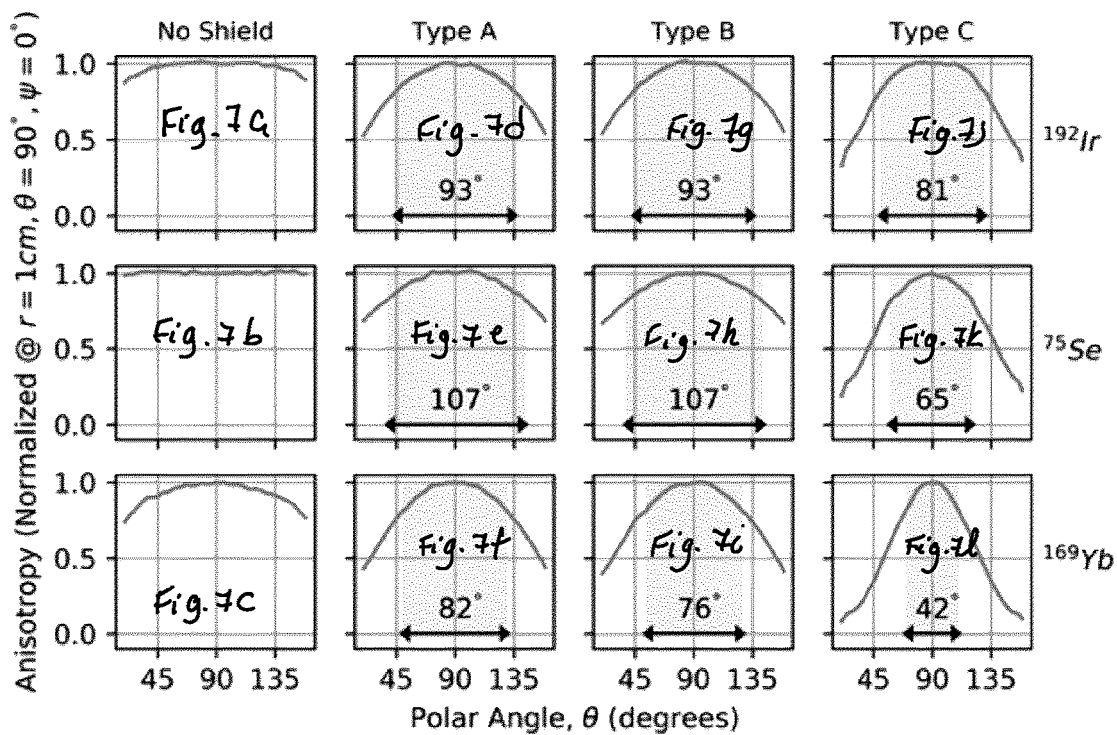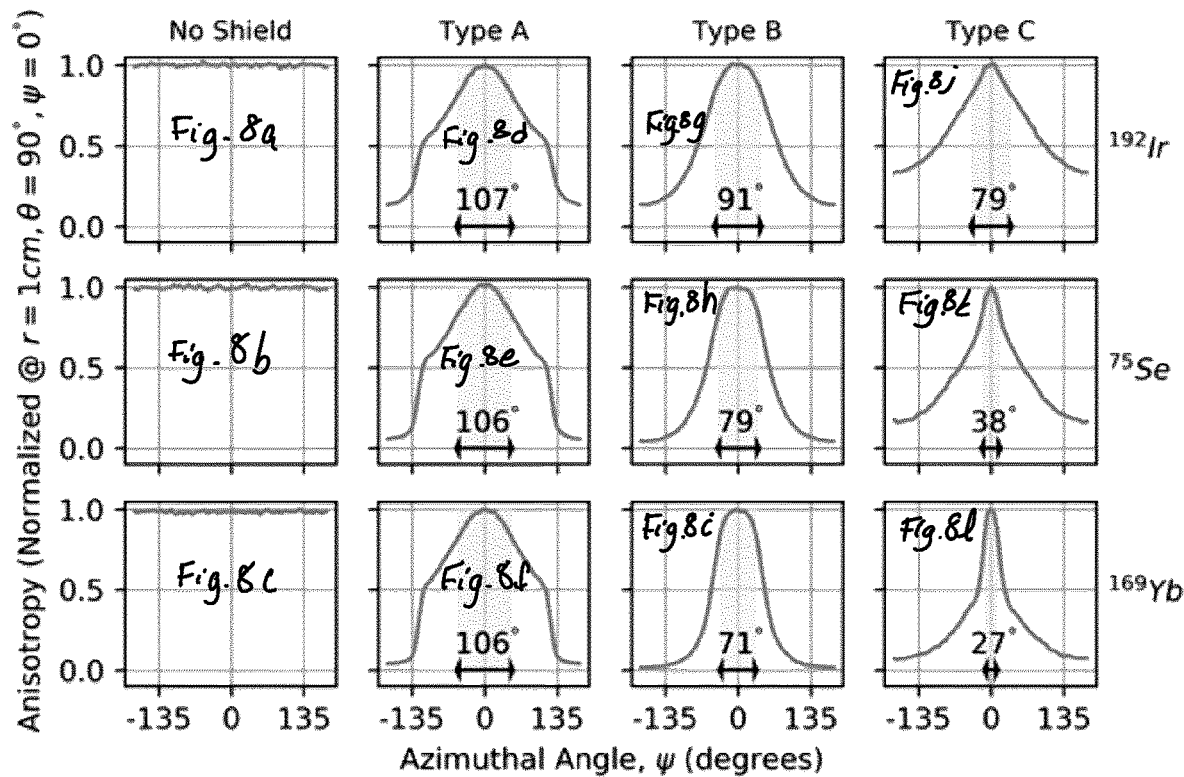

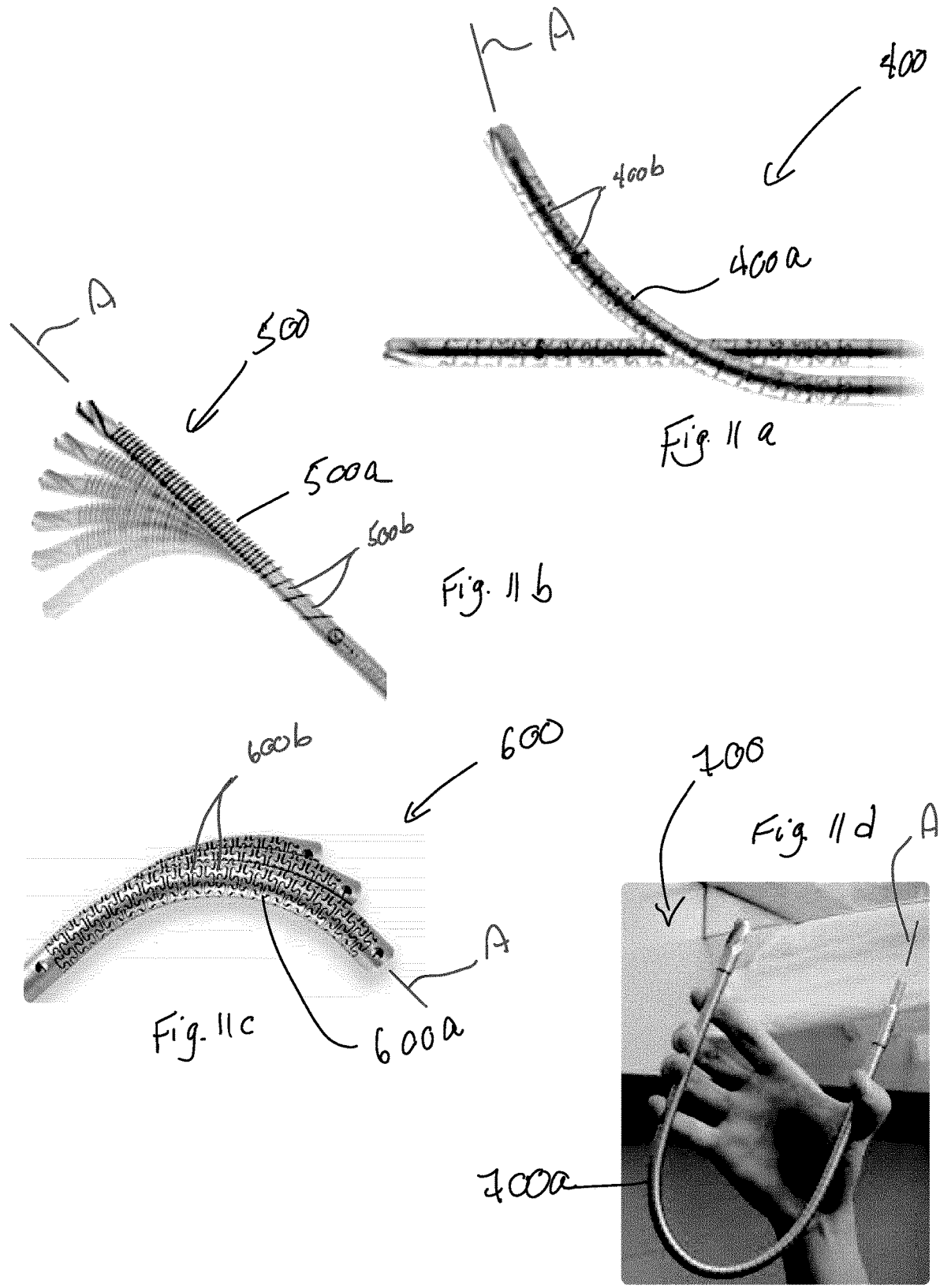

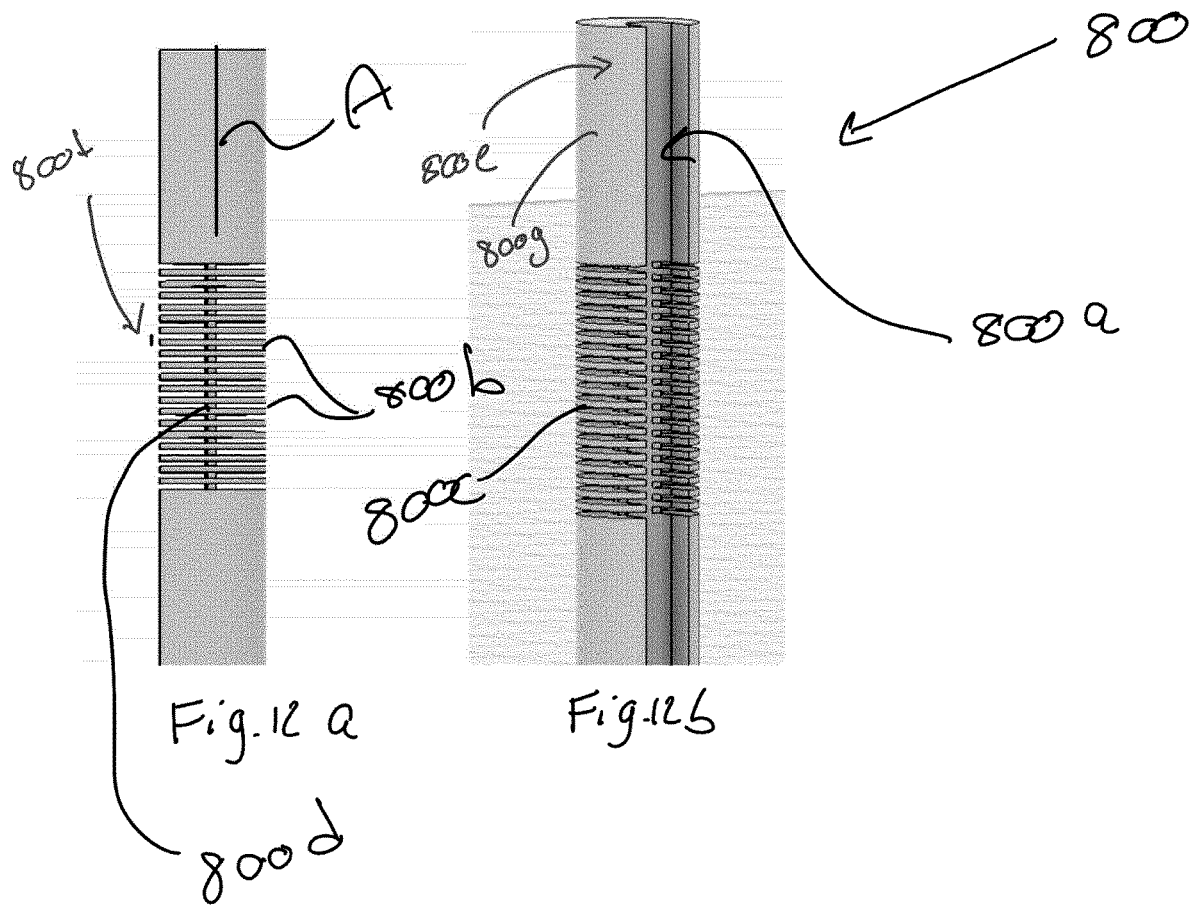

RADIATION SHIELDS FOR BRACHYTHERAPY

CROSS-REFERENCE TO RELATED APPLICATION

The present application claims priority on U.S. Patent Application No. 62/861,052 filed Jun. 13, 2019, the entire content of which is incorporated herein by reference.

TECHNICAL FIELD

The disclosure relates generally to apparatus and methods for radiation therapy, more particularly, to brachytherapy.

BACKGROUND

Radiation therapy is known to be an effective treatment for cancer. New technology developments in external beam radiation therapy during the last decades have led to improvements in tailoring the dose distribution to the shape of the tumour and minimizing the dose to organs at risk (OAR). However, location of the tumour within the organ, errors in treatment delivery because of incorrect patient positioning, large margins and tumour/patient movement during the treatment can result in excessive doses to organs at risk. Delivery of a specified dose requires more monitor units and, as a consequence, the total body dose due to leakage radiation can be increased. This may lead to dose escalation, conformation and sharp dose gradients on one hand, while conversely they may increase the integral dose exposure of healthy tissues, since larger volumes are exposed to low doses.

The use of external radiation therapy may be limited in cases where the proximity of the tumour to radiation sensitive normal tissues makes it difficult to obtain an optimal absorbed dose distribution in the tumours area. Brachytherapy is thus desirable in these circumstances. High dose rate brachytherapy is a form of radiation therapy where radiation is administered from radiation sources (radionuclides) directly into or near the tumour, giving a high radiation dose to the target volume while sparing the surrounding radiation sensitive healthy tissues. The radionuclides are administered using an afterloading technique, where the applicator is first placed into the tumour and the radioactive sources are loaded later by a machine known as an afterloader.

Magnetic resonance imaging (MRI) guided brachytherapy provides good dose distributions in the tumour, with decreased margins and toxicity, due to excellent delineation of the tumour and surrounding tissue. The steep dose gradient from brachytherapy sources results in improved therapeutic ratio compared with external beam radiation therapy for selected tumour sites. However, optimal dose distribution in the tumour is limited in many tumour sites due to the proximity of the tumour to organs at risk, such as the urethra, rectum, urinary bladder and neurovascular bundle for prostate cancer. Other organs at risk are skin and axilla for breast cancer, bladder, rectum, sigmoid, and vagina for cervical and uterine cancer, urethra, rectum, bone, and skin for vaginal and vulvar cancer, salivary glands and mandible for head and neck cancer, and lung and spine for oesophageal cancer.

IMBT, designed and delivered with accurate anatomic reference, has the objective to tailor treatments to each individual patient by treating all parts of the tumour without needlessly irradiating large regions of organs at risk. With MRI guided IMBT the oncologist can identify where the cancer has spread, and instead of treating a large area around the tumour, they can fit the cell-killing treatments to the tumour.

High dose rate brachytherapy (HDR-BT), especially with magnetic resonance (MR) image guidance, is one of the most effective and precise radiation delivery modalities with major impact on gynecological, genitourinary and prostate cancers. HDR-BT has been adopted rapidly in Canada, USA and Europe and is cost efficient compared to other treatment modalities. About 60% of the radiation oncology clinics across Canada offer this treatment modality with gynecologic, genitourinary and prostate cancers as the most commonly treated cancer sites. Due to the growing evidence of the benefits of HDR-BT and increasing number of cancer patients, the treatment modality has been successfully used on other cancer sites as well. In HDR-BT, encapsulated high activity radiation sources are temporary placed directly into or near localized tumours using needles, plastic catheters or other specialized applicators giving a high radiation dose to the tumour while the dose to sensitive organs at risk (OARs) surrounding the tumour is lower. However, radiation sources used in BT conventionally provide rotationally symmetric dose distributions, and deliver high dose to tumours with often poor target conformity due to the non-symmetrical shape of the tumours resulting in dose spillage to OARs.

SUMMARY

Brachytherapy is a targeted high-dose radiation treatment that can be delivered via radioactive seeds that are placed directly in or near the tumor or via an applicator device placed at the tumor site. Brachytherapy is an integral component of the treatment regimen of several localized and locally advanced cancers. Outcome in terms of disease control and radiation associated complications is a function of dose to the tumor and sensitive organs at risk (OARs). By utilizing an intensity modulated brachytherapy (IMBT) technique, dose delivery could be optimized to better conform to the tumor, enabling dose escalation while maintaining or reducing OARs doses. Herein, rotating shields, compatible with modern MRI-compatible intracavitary applicators, are disclosed. In certain embodiments these may be used, as an example only, for cervix and endorectal brachytherapy.

Three shield models are shown. In a particular embodiment, these shields are composed of platinum or tungsten, however other suitable materials may also be used. These shields might be used in conjunction with an $^{192}$Ir HDR source. Additionally, $^{75}$Se and $^{169}$Yb may be used as alternative gamma-ray emitting sources for IMBT.

In another aspect, different designs of flexible shields for brachytherapy are presented.

By incorporating metallic shields inside BT catheters, IMBT might open the possibility to escalate the dose to the tumour while more effectively shielding OARs by dynamically directing the radiation towards the target and away from the OARs, i.e., the dose distributions might better conform to the shape of the tumour. Dose escalation of the tumour might significantly improve the potential of HDR-BT while simultaneously reducing toxicity will increase quality of life of the patients and lead to improved therapeutic ratio and clinical outcomes.

Shields with an angular cut in the radial axis (and flexible longitudinally) are disclosed and might be used for vaginal, rectal cervix or any other intracavitary and intraluminal applicators.

The shields can either be solid, with cuts along the longitudinal axis making them flexible, or they can be flexible with cuts along the longitudinal axis and have an angular cut radially.

The shield can be standalone, i.e. a solid (no angular cuts in it, not connected to a rotating system) flexible, bendable rod that can be placed in an applicator or flexible, bendable with cut in any degree combined with a rotating system. The rotating shields can be controlled through a moving panel driven by a stepper motor. Sensors in the rotating mechanism will detect the position of the shield.

There is accordingly provided an intracavitary shield configured to be inserted inside a patient for brachytherapy, comprising: an elongated body having a central axis, the elongated body composed of a radiation-shielding material that is MRI-compatible; and a radioactive seed receiving cavity extending through or along the elongated body for slideably receiving a radioactive seed therein.

In the intracavitary shield as defined above, a center of the radioactive seed receiving cavity may be radially offset from the central axis of the elongated body.

In the intracavitary shield as defined above, the radiation-shielding material may be tungsten.

In the intracavitary shield as defined above, the radiation-shielding material may be platinum.

There is also provided an assembly configured to be inserted inside a patient for brachytherapy, comprising: an elongated body having a central axis, the elongated body composed of a radiation-shielding material that is MRI-compatible; and a radioactive seed receiving cavity extending through or along the elongated body for slideably receiving a radioactive seed therein, a center of the radioactive seed receiving cavity being radially offset from the central axis of the elongated body There is further provided an intracavitary shield configured to be inserted inside a patient for brachytherapy, comprising a flexible shield body formed by a plurality of shield sections interconnected to one another via flexible joints permitting relative movement between respective ones of the plurality of shield sections, each of the shield sections defining a cavity therein that is aligned with a corresponding cavity in an adjacent one of the plurality of shield sections, the cavities collectively forming a passage through which a radionuclide seed is slideably received.

In accordance with a first aspect, there is provided a radiation shield for an intensity modulated brachytherapy (IMBT) system, the radiation shield extending along a central axis and defining at least two radiation shield sections interconnected to one another and pivotable one relative to the other about an axis normal to the central axis, the at least two radiation shield sections defining radionuclide-receiving passages being circumferentially aligned with one another relative to the central axis for slideably receiving therein a radionuclide.

In accordance with the first aspect, the radiation shield may include a peripheral wall extending around the central axis, the peripheral wall defining a slit pattern.

Still in accordance with the first aspect, slits of the slit pattern may have a jigsaw shape or a helicoid shape.

Still in accordance with the first aspect, the radiation shield may include a monolithic body defining a flexible section, the flexible section including a plurality of slits, each of the slits extending from an outer face of the monolithic body toward the central axis, the slits ending at a core, discs defined between the slits and being axially spaced apart from one another to allow bending of the core.

Still in accordance with the first aspect, the at least two radiation shield sections may be interconnected to one another by a joint.

Still in accordance with the first aspect, the joint may include a ball protruding axially from an axial end face of one of the at least two radiation shield sections and a rounded cavity extending from an axial end face of the other of the at least two radiation shield sections, the ball received within the rounded cavity.

Still in accordance with the first aspect, the joint may include a tab protruding from an axial end face of one of the at least two radiation shield sections and a recess extending from the axial end face of the other of the at least two radiation shield sections, the tab pivotably received within the recess, the tab locked within the recess via a pin extending through a first aperture defined through the tab and through a second aperture defined through the other of the at least two radiation shield sections.

Still in accordance with the first aspect, the at least two radiation shield sections may be connected to one another via a flexible rod extending through registering apertures defined by the at least two radiation shield sections.

Still in accordance with the first aspect, the radionuclide-receiving passages may be grooves, bores, or cavities.

In accordance with a second aspect, there is provided a shield assembly for an intensity modulated brachytherapy (IMBT) system, comprising: a tubular applicator engageable to a rotating mechanism of the IMBT system, the tubular applicator having a peripheral wall enclosing an internal cavity extending longitudinally along a central axis; a radiation shield extending axially along the central axis and received within the internal cavity, the radiation shield made of an MRI-compatible and radiation attenuating material; and a radionuclide-receiving passage within the internal cavity of the tubular applicator, the radionuclide-receiving passage extending axially and being radially offset from the central axis.

The shield assembly and/or radiation shield thereof as described herein may further include, in whole or in part, one or more of the following additional features.

Still in accordance with the second aspect, the central axis may be free of intersection with the radionuclide-receiving passage.

Still in accordance with the second aspect, the radionuclide-receiving passage may be a groove defined by the radiation shield and extending axially along the central axis, the groove extending radially from an outer face of the radiation shield toward the central axis.

Still in accordance with the second aspect, the outer surface of the radiation shield may be convex but for the groove.

Still in accordance with the second aspect, the radionuclide-receiving passage may be defined between a cylindrical outer face of the radiation shield and the peripheral wall.

Still in accordance with the second aspect, a ratio of a diameter (Da) of the radiation shield to an internal diameter (D8) of the tubular applicator may be about 0.75.

Still in accordance with the second aspect, the radionuclide-receiving passage may be a bore extending through the radiation shield.

Still in accordance with the second aspect, the radiation shield may define apertures extending from an outer surface of the radiation shield to the bore, the apertures axially spaced-apart from one another along the central axis and being circumferentially aligned with one another.

Still in accordance with the second aspect, a ratio of a distance (D3) between a center of the bore and a center of the radiation shield to an internal diameter (D8) of the tubular applicator may range from 0.06 to 0.2.

Still in accordance with the second aspect, a ratio of a diameter (D7) of the bore to a the internal diameter (D8) of the tubular applicator may range from 0.09 to 0.3, wherein a ratio of a distance (d3) taken along the central axis between two adjacent ones of the apertures to the internal diameter of the tubular applicator may range from 0.6 to 2, and wherein a ratio of a diameter (D4) of the apertures to the internal diameter (D8) of the tubular applicator may range from 0.06 to 0.2.

Still in accordance with the second aspect, the MRI-compatible and radiation attenuating material may be tungsten.

Still in accordance with the second aspect, the MRI-compatible and radiation attenuating material may be platinum.

Still in accordance with the second aspect, the radiation shield may include at least two radiation shield sections interconnected to one another and pivotable one relative to the other about an axis normal to the central axis.

Still in accordance with the second aspect, the peripheral wall may define a slit pattern.

Still in accordance with the second aspect, slits of the slit pattern may have a jigsaw shape or a helicoid shape.

Still in accordance with the second aspect, the radiation shield may include a monolithic body defining a flexible section, the flexible section including a plurality of slits, each of the slits extending from an outer face of the monolithic body toward the central axis, the slits ending at a core, discs defined between the slits and being axially spaced apart from one another to allow bending of the core.

Still in accordance with the second aspect, the at least two radiation shield sections may be interconnected to one another by a joint.

Still in accordance with the second aspect, the joint may include a ball protruding axially from an axial end face of one of the at least two radiation shield sections and a rounded cavity extending from an axial end face of the other of the at least two radiation shield sections, the ball received within the rounded cavity.

Still in accordance with the second aspect, the joint may include a tab protruding from an axial end face of one of the at least two radiation shield sections and a recess extending from the axial end face of the other of the at least two radiation shield sections, the tab pivotably received within the recess, the tab locked within the recess via a pin extending through a first aperture defined through the tab and through a second aperture defined through the other of the at least two radiation shield sections.

Still in accordance with the second aspect, the at least two radiation shield sections may be connected to one another via a flexible rod extending through registering apertures defined by the at least two radiation shield sections.

In accordance with a third aspect, there is provided an intensity modulated brachytherapy (IMBT) system, comprising a rotating system and a shield assembly drivingly engaged to the rotating system for rotating the shield assembly about a central axis thereof, the shield assembly having: a tubular applicator including a peripheral wall enclosing an internal cavity extending axially along the central axis; a radiation shield within the internal cavity and extending axially along the central axis, the radiation shield made of an MRI-compatible and radiation attenuating material; and a radionuclide-receiving passage within the internal cavity of the tubular applicator, the radionuclide-receiving passage being eccentric relative to the internal cavity of the tubular applicator.

The intensity modulated brachytherapy (IMBT) system and/or radiation shield thereof as described herein may further include, in whole or in part, one or more of the following additional features.

Still in accordance with the third aspect, the shield assembly may be pivotably connected to the rotating system via a joint.

Still in accordance with the third aspect, the joint may be a U-joint.

Still in accordance with the third aspect, the rotating system may include a motor in driving engagement with a shaft, the shaft drivingly engaged to the shield assembly.

Still in accordance with the third aspect, the central axis may be free of intersection with the radionuclide-receiving passage.

Still in accordance with the third aspect, the radionuclide-receiving passage may be a groove defined by the radiation shield and extending axially along the central axis, the groove extending radially from an outer face of the radiation shield toward the central axis, the groove sized to slidably receive therein a radionuclide.

Still in accordance with the third aspect, a depth of the groove taken in a radial direction relative to the central axis may be greater than a diameter of the radionuclide.

Still in accordance with the third aspect, the radionuclide-receiving passage may be defined between a cylindrical outer face of the radiation shield and the peripheral wall.

Still in accordance with the third aspect, a ratio of a diameter (Da) of the radiation shield to an internal diameter (D8) of the tubular applicator may be about 0.75.

Still in accordance with the third aspect, the radionuclide-receiving passage may be a bore extending through the radiation shield axially along the central axis.

Still in accordance with the third aspect, the radiation shield may define apertures extending from an outer surface of the radiation shield to the bore, the apertures axially spaced-apart from one another along the central axis and being circumferentially aligned with one another.

Still in accordance with the third aspect, a ratio of a distance (D3) between a center of the bore and a center of the radiation shield to an internal diameter (D8) of the tubular applicator may range from 0.06 to 0.2.

Still in accordance with the third aspect, a ratio of a diameter (D7) of the bore to a the internal diameter (D8) of the tubular applicator may range from 0.09 to 0.3, wherein a ratio of a distance (d3) taken along the central axis between two adjacent ones of the apertures to the internal diameter of the tubular applicator may range from 0.6 to 2, and wherein a ratio of a diameter (D4) of the apertures to the internal diameter (D8) of the tubular applicator may range from 0.06 to 0.2.

Still in accordance with the third aspect, the MRI-compatible and radiation attenuating material may be tungsten.

Still in accordance with the third aspect, the MRI-compatible and radiation attenuating material may be platinum.

Still in accordance with the third aspect, the radiation shield may include at least two radiation shield sections interconnected to one another and pivotable one relative to the other about an axis normal to the central axis.

Still in accordance with the third aspect, the peripheral wall may define a slit pattern.

Still in accordance with the third aspect, slits of the slit pattern may have a jigsaw shape or a helicoid shape.

Still in accordance with the third aspect, the radiation shield may include a monolithic body defining a flexible section, the flexible section including a plurality of slits, each of the slits extending from an outer face of the monolithic body toward the central axis, the slits ending at a core, discs defined between the slits and being axially spaced apart from one another to allow bending of the core.

Still in accordance with the third aspect, the at least two radiation shield sections may be interconnected to one another by a joint.

Still in accordance with the third aspect, the joint may include a ball protruding axially from an axial end face of one of the at least two radiation shield sections and a rounded cavity extending from an axial end face of the other of the at least two radiation shield sections, the ball received within the rounded cavity.

Still in accordance with the third aspect, the joint may include a tab protruding from an axial end face of one of the at least two radiation shield sections and a recess extending from the axial end face of the other of the at least two radiation shield sections, the tab pivotably received within the recess, the tab locked within the recess via a pin extending through a first aperture defined through the tab and through a second aperture defined through the other of the at least two radiation shield sections.

Still in accordance with the third aspect, the at least two radiation shield sections may be connected to one another via a flexible rod extending through registering apertures defined by the at least two radiation shield sections.

BRIEF DESCRIPTION OF THE DRAWINGS

Reference is now made to the accompanying figures in which:

FIG. 1b is an enlarged view of zone 1b-1b on FIG. 1a;

FIG. 2b is a schematic cross-sectional view of the intracavitary shield of FIG. 2a;

FIG. 2c is a schematic front three dimensional view of the intracavitary shield of FIG. 2a;

FIG. 3a is a schematic top three dimensional view of an intracavitary shield in accordance with another embodiment;

FIG. 3b is a schematic cross-sectional view of the intracavitary shield of FIG. 3a;

FIG. 3c is a schematic front three dimensional view of the intracavitary shield of FIG. 3a;

FIG. 4a is a schematic top three dimensional view of the intracavitary shield of FIG. 1a;

FIG. 4b is a schematic cross-sectional view of the intracavitary shield of FIG. 4a;

FIG. 4c is a schematic front three dimensional view of the intracavitary shield of FIG. 4a;

FIGS. 5a to 5l are axial cross-sectional views of Monte Carlo (MC) calculated doses for a non-shielded tandem (FIGS. 5a to 5c) and for the rotating shields of FIG. 2a (FIGS. 5d to 5f), FIG. 3a (FIGS. 5g to 5i), and FIG. 4a (FIGS. 5j to 5l) using $^{192}$Ir (FIGS. 5a, 5d, 5g, 5j), $^{75}$Se (FIGS. 5b, 5e, 5h, 5k), and $^{169}$Yb (FIGS. 5c, 5f, 5i, 5l) as radionuclides;

FIGS. 6a to 6l are longitudinal cross-sectional views of Monte Carlo (MC) calculated doses for a non-shielded tandem (FIGS. 6a to 6c) and for the rotating shields of FIG. 2a (FIGS. 6d to 6o, FIG. 3a (FIGS. 6g to 6i), and FIG. 4a (FIGS. 6j to 6l) using $^{192}$Ir (FIGS. 6a, 6d, 6g, 6j), $^{75}$Se (FIGS. 6b, 6e, 6h, 6k), and $^{169}$Yb (FIGS. 6c, 6f, 6i, 6l) as radionuclides;

FIGS. 7a to 7l are polar anisotropy graphs taken at a radial distance of 1 cm and normalized a radial distance of 1 cm, a polar angle of 90 degrees and an azimuthal angle of 0 degree, for a non-shielded tandem (FIGS. 7a to 7c) and for the rotating shields of FIG. 2a (FIGS. 7d to 7f), FIG. 3a (FIGS. 7g to 7i), and FIG. 4a (FIGS. 7j to 7l) using $^{192}$Ir (FIGS. 7a, 7d, 7g, 7j), $^{75}$Se (FIGS. 7b, 7e, 7h, 7k), and $^{169}$Yb (FIGS. 7c, 7f, 7i, 7l) as radionuclides;

FIGS. 8a to 8l are azimuthal anisotropy graphs taken at a radial distance of 1 cm and normalized a radial distance of 1 cm, a polar angle of 90 degrees and an azimuthal angle of 0 degree, for a non-shielded tandem (FIGS. 8a to 8c) and for the rotating shields of FIG. 2a (FIGS. 8d to 8o, FIG. 3a (FIGS. 8g to 8i), and FIG. 4a (FIGS. 8j to 8l) using $^{192}$Ir (FIGS. 8a, 8d, 8g, 8j), $^{75}$Se (FIGS. 8b, 8e, 8h, 8k), and $^{169}$Yb (FIGS. 8c, 8f, 8i, 8l) as radionuclides;

FIGS. 11a to 11d are schematic views of flexible intracavitary shields shown in different positions in accordance with possible embodiments;

FIGS. 12a and 12b are schematic front and three dimensional views of a flexible intracavitary shield in accordance with another embodiment;

DETAILED DESCRIPTION

Figure 1A:
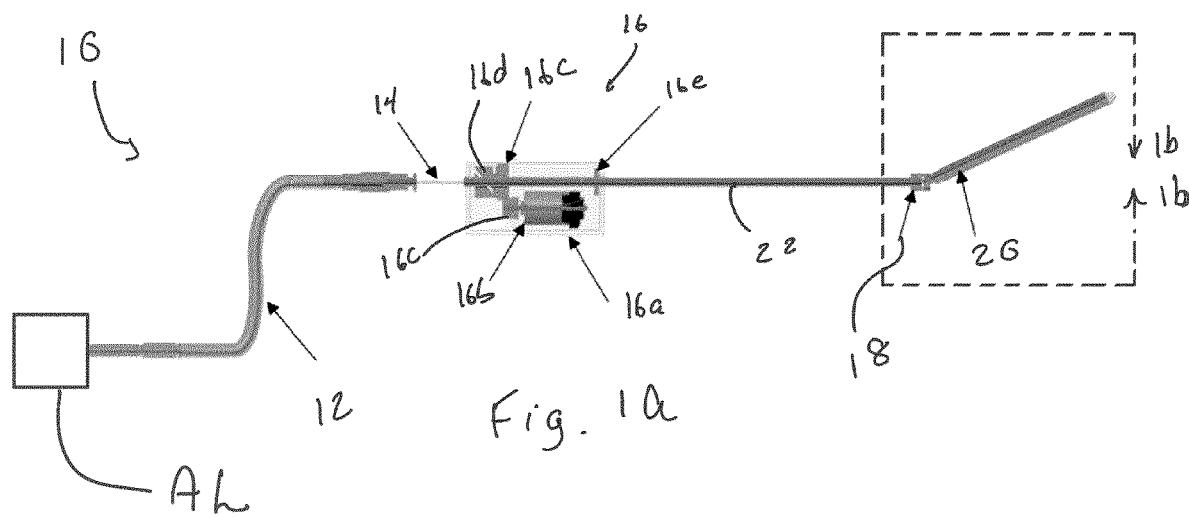
FIG. 1a is a schematic partially transparent view of an intensity modulated brachytherapy (IMBT) system in accordance with one embodiment.

In interstitial high dose rate brachytherapy (HDR-BT), a radionuclide, also referred to as a radioactive seed, is temporarily placed via thin catheters inside or in close proximity of the tumor (for example, prostate, breast, head & neck or cervix cancers). The catheters are then connected to an HDR afterloader, which is a machine that contains a single highly radioactive (e.g., $^{192}$Ir) source at the end of a wire. This technique is referred to as a remote afterloading technique. The source may be pushed into each of the catheters, one by one under computer control and guided to the tumour site. The computer controls how long the source stays in each catheter (dwell time), and where along the catheter, inside or close to the tumour, it should pause to expose its radiation (dwell positions). With a few well-placed catheters in the tumor, HDR-BT may provide a precise treatment taking only a few minutes. After the desired dose is delivered, the radiation source is returned back to the afterloader and the catheters are removed.

HDR-BT with remote afterloading is also performed with intracavitary or intraluminal BT. In intracavitary BT the radionuclide is placed in a special applicator inside a body cavity (for example for treatment of gynecological and rectal cancers). In intraluminal BT the radionuclide is placed in a special applicator inside a body passage and guided to the tumour site (esophageal or lung cancers).

HDR-BT has proven to increase overall survival for cervical and rectum cancer patients with even further overall survival benefit when moving to image-guided BT. However, optimal dose distribution in the tumour is limited for many tumour sites treated with HDBT due to the proximity of the tumour to organs at risk (OARs) such as urethra, rectum, urinary bladder and neurovascular bundle for prostate cancer, skin and axilla for breast cancer, bladder, rectum, sigmoid, and vagina for cervical and uterine cancer, urethra, rectum, bone, and skin for vaginal and vulvar cancer, salivary glands and mandible for head & neck cancer and lung and spine for oesophageal cancer. These cancer sites may benefit from intensity modulated brachytherapy (IMBT) since the radiation dose may be directed towards the target and away from OARs. In BT, the dose is prescribed to an isodose encompassing a small target volume.

Again, clinical studies have shown that dose escalation for locally advanced cervical cancer under image-guided HDR-BT can lead to increased local control. However, for conventional intracavitary HDR-BT dose to bladder, rectum and sigmoid may limit the maximum dose deliverable to the tumour due to the fixed geometry of the applicators and the symmetrical shape of the dose distribution. The tumour is not symmetrically shaped, all parts of the planning target volume will not receive the prescribed dose, while large volume of bladder, rectum and sigmoid may be overdosed. The ability to produce anisotropic dose distributions from individual dwell positions might allow for protection of OARs from excessive dose without compromising target coverage in many cancer sites treated with HDR-BT. IMBT might allow for the placing of dwell positions very close to the OARs, irradiating larger volume and escalating the dose inside the tumour while shielding the OARs.

Intracavitary and intraluminal applicators can be straight or bend with up to 45 degrees to effectively treat a variety of anatomies. Different configurations of straight and flexible shields prototypes are discussed herein below.

IMBT Delivery System

Figure 1B:
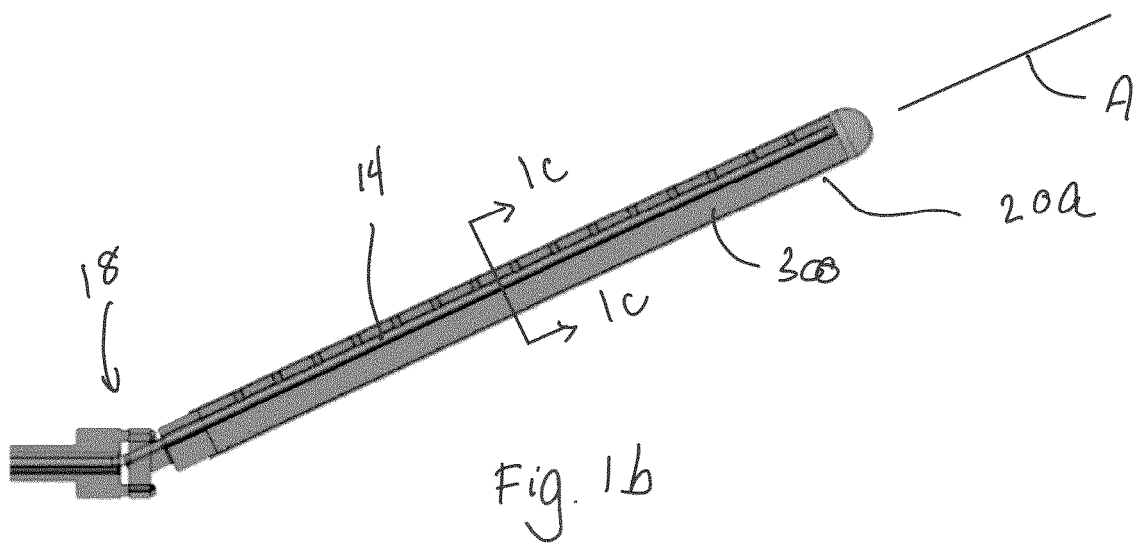
Figure 1C:
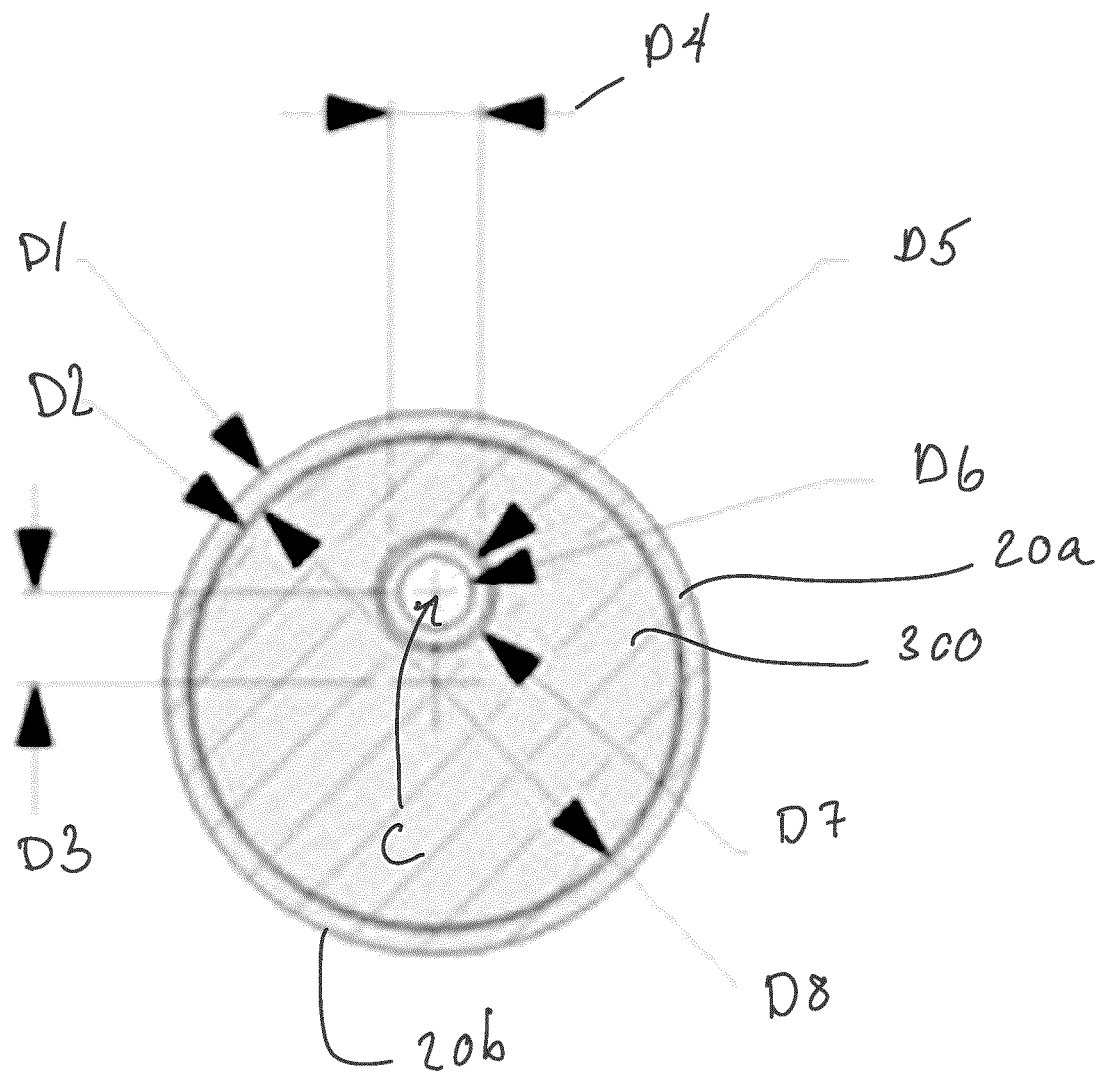
FIG. 1c is a schematic cross-sectional view of a shield assembly of the IMBT system of FIG. 1a taken along line 1c-1c on FIG. 1b.

Referring to FIGS. 1a to 1c, an IMBT delivery system is shown generally at 10. While the system 10 may be adapted for cervix cancer applications, it is to be understood that its feature and the system as whole may alternately be used for other cancer applications. The system 10 includes an afterloader connection 12 connectable to an afterloader AL containing a source of an isotope for treating tumors. A needle 14 is connected to the afterloader connection 14 and is used to receive therein a radionuclide from the afterloader. The system 10 includes a rotating mechanism 16, a joint assembly 18, and a shield assembly 20.

The rotating mechanism 16 is used for rotating the shield assembly 20 about its central axis A. As will be described herein below, different shields may be used. The shields are used to allow radiation to radiate from the radionuclide toward a tumor in a certain orientation and to attenuate radiation in other orientations to limit radiation from radiating organs at risk (OAR).

In the depicted embodiment, the rotating mechanism 16 includes a casing 16a enclosing a motor 16b and a gearbox 16d having a plurality of gears 16c. The gears 16c are drivingly engaged by the motor 16a, which is herein an electric motor, and are engaged to the shield assembly 20 for rotating the same about the central axis A. An angular sensor 16e is located within the casing 16a and operatively connected to shield assembly 20 for determining an angular position of the shield assembly 20.

The shield assembly 20 is in driving engagement with the electric motor 16a via a driving shaft 22. The driving shaft 22 is connected to the shield assembly 20 via the joint assembly 18, which is herein a U-joint. More details about the delivery system 10 are presented in Famulari G, Enger S A. A novel intensity modulated high dose rate brachytherapy delivery system with 169 Yb. Int J Radiat Oncol 2017; 99(2):E657; and in Famulari G, Enger S A. Intensity modulated brachytherapy system for dynamic modulation of shielded catheters. Radiother Oncol 2018; 127:S90, and in U.S. patent application Ser. No. 16/471,703, the entire contents of which are presented herein by reference.

Referring now to FIGS. 1b-1c, the shield assembly 20 includes a rotating shield 300 received within a tube 20a, also referred to as a tandem or a tubular applicator. The tandem 20a has a peripheral wall 20b enclosing an internal cavity 20c extending longitudinally along the central axis A. The shield 300 is received within the internal cavity 20c and is made of an MRI-compatible material, such as platinum or tungsten. Although the shield assembly 20 is shown with the shield 300 described below with reference to FIGS. 4a to 4c, the shield assembly 20 may include any of the shields described below with reference to FIGS. 2a to 3c and FIGS. 11a to 17b.

In the embodiment shown, the MRI/CT-compatible tandem and ring applicator (Elekta Brachytherapy, Veenendaal, The Netherlands) was redesigned to enable rotating shield IMBT. Brachytherapy cervix applicators are typically built such that they have a tandem/ring or tandem ovoids. The ring extends annularly around the tandem 20a. The ovoids are two oval volumes on each side of the tandem 20a. In one particular embodiment, the clinical tandem 20a has a 6 mm outer diameter D1 and an inner diameter close to 3 mm. To maximize the amount of shielding material in the tandem 20a, the applicator was redesigned with an inner diameter D8 of 5.4 mm. The ring is unshielded and is left unchanged. For the purpose of this study, the tandem casing material having a thickness of 0.3 mm is considered to be water equivalent.

Straight Shields Prototypes

Shields were modeled to fit inside the redesigned MRI/CT-compatible tandem 20a, which has an inner diameter D8 of 5.4 mm, and connect to the IMBT delivery system 10 described above via the joint assembly 18, which enables the transfer of rotational force while maintaining the bend required for the angled tandem. The shields have a single channel that may maximize an amount of attenuating material within the tandem 20a and is possible due to the rotational IMBT delivery system 10. All shield designs disclosed herein below are based on a solid cylinder.

Tungsten is used herein as a shield material due its relative high density and low magnetic susceptibility. Tungsten and its non-iron alloys may strike a balance between affordability and manufacturability. It will be appreciated that any suitable shielding material may be used without departing from the scope of the present disclosure. For instance, the shielding material may be platinum. The shield is a radiation shield made of an MRI-compatible material that is also radiation attenuating (i.e. it substantially prevents radiation from being able to pass therethrough).

Referring to FIGS. 2a to 4c, three rotating intracavitary shields are designed. The shields are designed to fit inside the intrauterine tandem 20a described above and having an external diameter D1 of about 6 mm. This tandem is commonly used in the treatment of locally advanced cervical cancer. As will be described below, each of the shield assemblies defines a radionuclide-receiving passage C, or channel, within the internal cavity of the tandem 20a. In all cases, the radionuclide-receiving passages C are radially offset from the central axis A. In other words, those passages C are eccentric with the internal cavity 20c tandem 20a. This may allow the dose to be anisotropic such that a higher dose is delivered to the tumor while shielding the OARs. In the depicted embodiments, the central axis A is free of intersection with the radionuclide-receiving passage C.

All three shields may be compatible with a rotating IMBT delivery system as disclosed in international patent application published under number WO 2018/112625, the entire content of which is incorporated herein by reference.

The disclosed IMBT shields may enable radial dose modulation with a single channel in the shield. When compared to static multichannel shields, the disclosed shields might permit more shielding material to fit inside the intracavitary applicator, thereby enhancing the modulation capacity.

The radionuclide-receiving passage diameter D7 for all shields 100, 200, 300 is 1.33 mm. All shields are 8 cm long for compatibility with the longest tandem size. For the conventional, non-shielded tandem, the radionuclide-receiving passage was placed in the center.

Figure 2A:
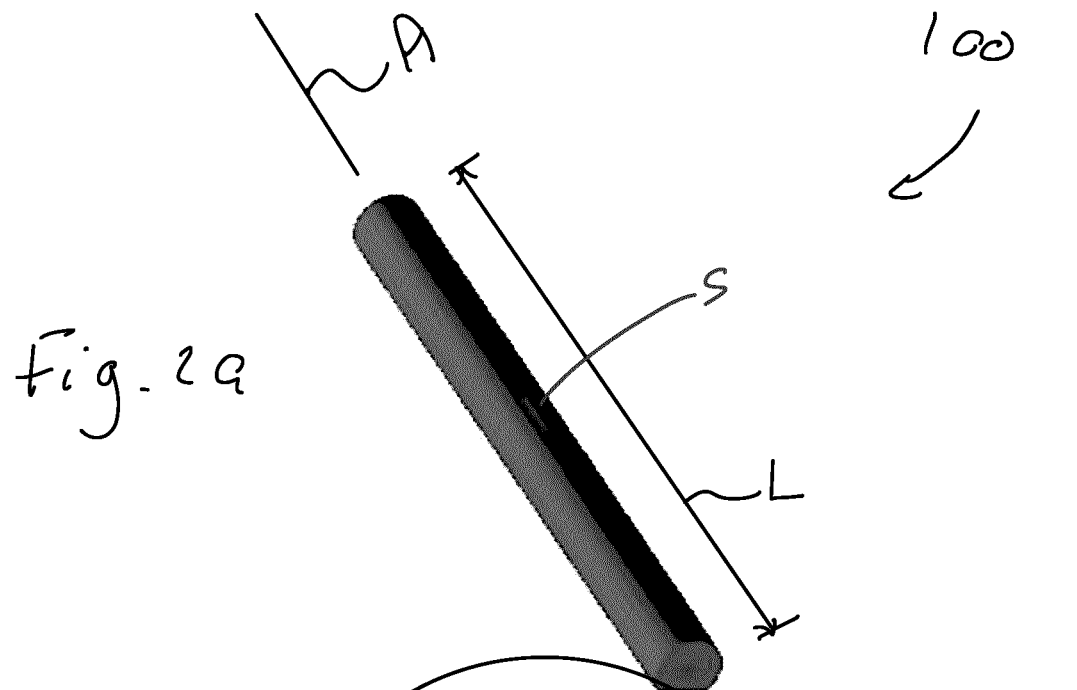
FIG. 2a is a schematic top three dimensional view of an intracavitary shield in accordance with one embodiment.
Figure 2B:
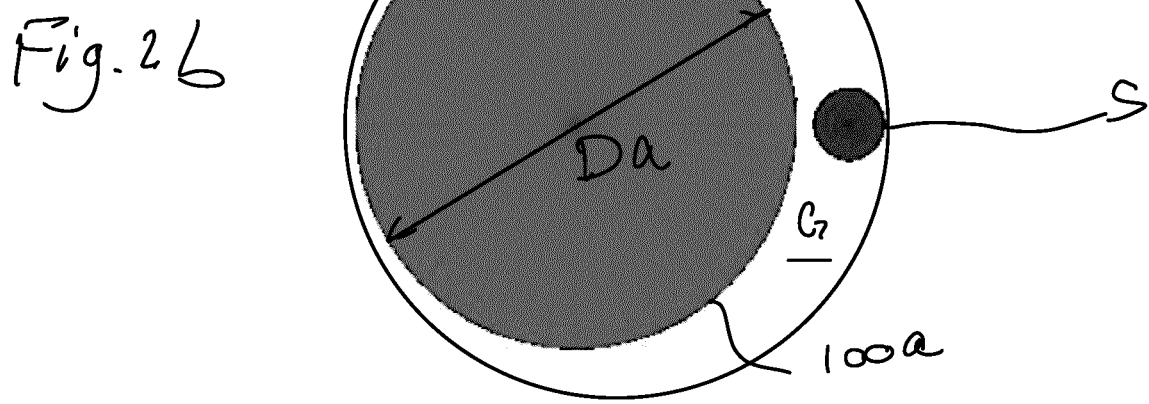
Figure 2C:
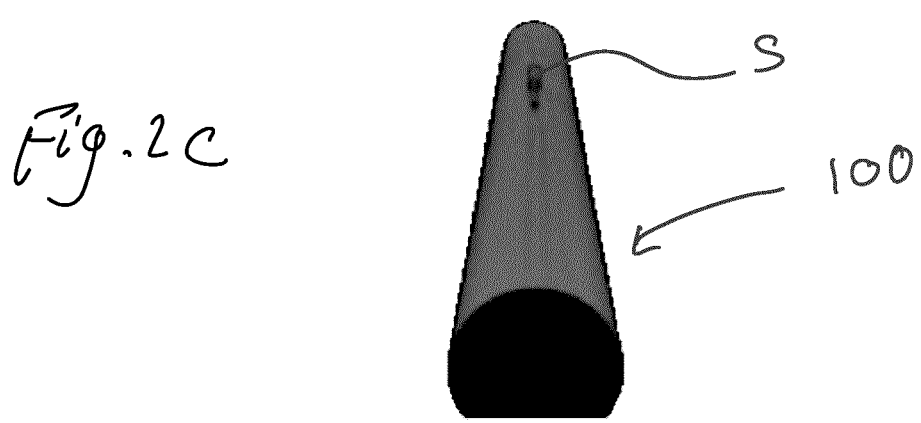

Referring to FIGS. 2a to 2c, a shield in accordance with one embodiment is shown generally at 100. This shield is referred to herein below as the type-A shield 100. The type-A shield 100 is a solid cylinder having a diameter Da of about 4.07 mm. In the embodiment shown, a ratio of a diameter (Da) of the radiation shield to an internal diameter (D8) of the tubular applicator is about 0.75.

The shield 100 is radially offset from the radionuclide-receiving passage C. In the embodiment shown, the radionuclide-receiving passage C is located radially outwardly of an outer surface 100a of the type-A shield 100 relative to the central axis A. The radionuclide-receiving passage C is defined between the outer face 100a of the shield 100 and the peripheral wall 20b of the tandem 20a; the wall 20b is shown in FIG. 2b for easier understanding. The shield 100 and the tandem 20a are spaced-apart from one another such that an annular gap G between the shield 100 and the peripheral wall 20b of the tandem 20a has a radial thickness being non-axisymmetric. The radionuclide-receiving passage C is herein located at a circumferential position where the radial thickness of the annular gap G is maximal. In the present case, upon rotation of the shield assembly 20 via the rotating mechanism 16, the type-A shield 100 and the radionuclide rotate around each other within the tandem 20a (FIG. 1a).

Referring to FIGS. 3a to 3c, a shield in accordance with another embodiment is shown generally at 200 and is referred to as the type-B shield herein below. The type-B shield 200 is a solid cylindrical shield having a diameter db of 5.4 mm to fit inside the tandem 20a and has a single groove 202 extending radially from an outer face 200a of the shield 200 toward the central axis A. The radionuclide-receiving passage C is defined by the groove 202. The groove 202 extends along the central axis A and parallel thereto. A depth H of the groove 202 taken in a radial direction relative to the central axis A is greater than a diameter of the radionuclide S. In the embodiment shown, the shield is free of another groove. The outer surface 200a is convex but for the groove 202.

In the embodiment shown, the groove 202 has a straight portion that extends from the outer surface 200a of the shield 100 and a circular portion that extends from the straight portion. As shown, the radionuclide, when received in the groove 202, do not protrude radially beyond the outer surface 200a of the shield 100. The groove 202 may extend along the entire length L of the type-B shield 200 and along the central axis A.

It will be appreciated that the shield 200 may be used to treat other cancers, such as but not limited to rectal cancer. Dimensions of the shield 200 are adjusted in accordance with the type of cancer to treat. For rectal application, the shield 200 may have a diameter of about 15 mm. The groove 202 may have a depth extending radially relative to the central axis A of about 4.33 to about 4.45 mm and a width in a direction normal to the depth of about 1.33 mm. The length of the shield may be 80 mm. The radionuclide may be located 4.5 mm from the outer face 200a of the shield 200. The shield used for rectal cancer may have a emission window of up to 45 degrees. The shield may be flexible and thicker than the above dimensions by about 5 mm. This shield may also be used for vaginal and endometrial cancers.

Three endorectal HDR-BT brachytherapy cases with high-risk-CTV (HR-CTV) ranging between 5.1-13.7 cm$^3$, were planned and optimized in RapidBrachyMC-TPS, a MC-based research TPS. Shield rotations were limited to 10-degree increments. The contralateral, uninvolved rectal D50 was compared by normalizing the clinical and IMBT plans such that CTV D90 received 6.5 Gy per fraction.

Mean treatment times were 2.1±0.6 min and 15.1±3.3 min for clinical and IMBT, respectively. IMBT may reduce the uninvolved rectum D50 by 55.5±3.9% relative to conventional HDR-BT. Similarly, IMBT may improve CTV D98 by 12.4±5.5%. This may show that dynamic shield IMBT applicator for endorectal brachytherapy may be capable of improving healthy tissue sparing while improve target coverage.

Referring now to FIGS. 4a to 4c, a shield in accordance with another embodiment is shown generally at 300 and is referred to below as the type-C shield. The type-C shield 300 defines a longitudinal bore 302 defining the radionuclide-receiving passage C. The bore 302 has a center radially offset from a center of the shield 300 by a distance D3 (FIG. 1c) of 1 mm relative of the central axis A. In the embodiment shown, a ratio of a distance (D3) between a center of the bore 302 and a center of the radiation shield 300 to an internal diameter (D8) of the tubular applicator is about 0.19. The shield 300 is shown installed into the tandem 20a in FIG. 1c. The type-C shield 300 is similar to a flute due to the beam collimations. The type-C shield 300 defines a plurality apertures or holes 300b having a diameter D4 of 1 mm and being axially spaced apart from another relative to the central axis A by a distance d3 of 10 mm. The diameter D4 of the apertures 300b is less than that of the bore 302. In the embodiment shown, all of the holes 300b are circumferentially aligned with one another relative to the central axis A. In the embodiment shown, the diameter D4 of the spaced apart apertures 300b is less than the diameter D7 (FIG. 1c) of the bore 302. In the embodiment shown, a ratio of a diameter (D7) of the bore 302 to a the internal diameter (D8) of the tubular applicator 20a is about 0.25, a ratio of a distance (d3) taken along the central axis A between two adjacent ones of the apertures 300b to the internal diameter (D8) of the tubular applicator 20a is about is about 1.85, and a ratio of a diameter (D4) of the apertures 300b to the internal diameter (D8) of the tubular applicator is about 0.19.

In some cases, the shield 100, 200, 300 may have a diameter of from 5 to 15 mm. Therefore, a ratio of a distance (D3) between a center of the bore 302 and a center of the radiation shield 300 to an internal diameter (D8) of the tubular applicator may range from 0.06 to 0.2. In the embodiment shown, a ratio of a diameter (D7) of the bore 302 to a the internal diameter (D8) of the tubular applicator 20a may range from 0.09 to 0.3, a ratio of a distance (d3) taken along the central axis A between two adjacent ones of the apertures 300b to the internal diameter (D8) of the tubular applicator 20a may range from 0.6 to 2, and a ratio of a diameter (D4) of the apertures 300b to the internal diameter (D8) of the tubular applicator is about 0.06 to 0.2. The diameter D1 of the tandem 20 ranges from 5 to 6 mm.

Each of the disclosed shields has only a single radionuclide-receiving passage C. This allows to maximize an amount of shielding material (e.g., tungsten) within the tandem 20a, which has a fixed size. The rotating mechanism 16 allows to rotate the shield assembly to direct the radiation towards the tumors while having the shielding material to protect the OAR. The ability to rotate the shield assembly 20 and to shield the OAR may allow to use higher radiation dose for treating the tumor while minimizing damage to OAR.

For uterus applications, the length of the shields is selected such that it may match a length of a patient's uterus. For instance, a 7 cm long tandem is used for a 7 cm deep uterus. This matching length corresponds to that of a therapeutic portion of the tandem, that is, the portion received in the patient. For uterus application, the diameter of the tandem ranges from 5 to 6 mm. For cervix applications, the diameter of the shield is as large as possible and may be the same as that of the tandem 20a minus 0.5 to 0.9 mm.

Monte Carlo Simulations

The simulated HDR source was modeled after the Flexisource used in the Elekta Flexitron afterloader (Elekta Brachytherapy, Veenendaal, The Netherlands). The active core (radionuclide) is a cylinder with 0.6 mm diameter and 3.5 mm length. The active core material was set to $^{192}$Ir, $^{75}$Se or $^{169}$Yb. The active core was encapsulated by stainless-steel-304 with outer dimensions of 4.6 mm length and 0.85 mm diameter. The drive cable is also composed of stainless-steel-304 and is modeled with a length of 5 mm.

Simulations were performed using a Monte Carlo based treatment planning software (RapidBrachyMCTPS with Geant4 MC toolkit). Herein, decay events were simulated for each radionuclide. $^{192}$Ir which has approximately 2.3 photons per decay event would lead to a simulation with 2.3×108 primary photons. Similarly $^{75}$Se and $^{169}$Yb generate approximately 2.3 and 3.8 photons per decay, respectively. Penelope low-energy electromagnetic physics list was used to simulate electromagnetic interactions. Due to the low photon energies emitted from the simulated radionuclides, dose was approximated by the collisional kerma and scored using a track length estimator. Parallel world formalism implemented in Geant4 was used for scoring with the resolution of the scoring grid being 1 mm$^3$. The source-shield geometry was placed in the center of a (50 cm)3 water phantom. A single dwell position located halfway up the 8 cm long intrauterine shield was simulated for all shield types and simulated radionuclides. The source was oriented in the positive-z direction. The tandem is centered at the origin. In the spirit of TG-43, the polar angle (also known as the zenith angle) measured from the z-axis is denoted as θ. We define ψ to be the azimuthal angle in the x-y plane and is the axis of rotation for dose modulation. The radius, r, is defined as the distance from the origin. To quantitatively evaluate the attenuation capacity of each shield-radionuclide combination, the transmission factor TF is calculated and defined as:

$$TF = \frac{D(r = 1 \text{ cm}, \theta = 90°, \psi = 180°)}{D(r = 1 \text{ cm}, \theta = 90°, \psi = 0°)}$$

where TF is the ratio of the dose at 1 cm from the center of the tandem on the x-y plane of the shielded side to the unshielded side. The emission window is at an azimuthal angle of 0°.

Results

Referring now to FIGS. 5a to 5l and to FIGS. 6a to 6l, graphs of dose distributions are presented and are normalized at a radius of 1 cm from the central axis A, a polar angle of 90 degrees and an azimuthal angle of 0 degree. The transmission factors are summarized in the table below.

TABLE 1

|  | Type A | Type B | Type C |
| --- | --- | --- | --- |
| $^{192}$Ir | 13.1% ± 0.4% | 12.9% ± 0.4% | 32.2% ± 0.4% |
| $^{75}$Se | 4.2% ± 0.7% | 4.0% ± 0.8% | 16.1% ± 0.6% |
| $^{169}$Yb | 1.8% ± 1.2% | 1.2% ± 1.5% | 6.4% ± 1.3% |

FIGS. 5a to 5c, 6a to 6c, 7a to 7c, and 8a to 8c show the dose distributions for a tandem devoid of a shielding material. Those graphs show that the dose distributions is substantially isotropic. FIGS. 5d to 5l, 6d to 6l, 7d to 7l, and 8d to 8l show that the shielding material allows to create an anisotropy in the dose distributions.

The normalized polar and azimuthal anisotropies are shown in FIG. 5 and FIG. 6. Beam widths, defined as the full width at 80% maximum in the polar direction (evaluated at r=1 cm, =0°) are annotated on the subplots of FIG. 7. Similarly, beam widths in the azimuthal direction (evaluated at r=1 cm, =90°) are annotated in FIG. 8.

To quantify dose homogeneity, which is the ratio of the volume receiving at least 200% of the prescribed dose to the volume receiving at least 100% of the prescribed dose is calculated for all cases. Dose in voxels which are inside the tandem are excluded to assess dose homogeneity the patient is exposed to. Dose homogeneities for all shield-radionuclide combinations are summarized in Table 2.

TABLE 2

|  | No Shield | Type-A | Type-B | Type-C |
| --- | --- | --- | --- | --- |
| $^{192}$Ir | 0.31 | 0.33 | 0.33 | 0.29 |
| $^{75}$Se | 0.30 | 0.32 | 0.34 | 0.29 |
| $^{169}$Yb | 0.31 | 0.33 | 0.35 | 0.27 |

The results presented herein show that all three radionuclides are viable sources for the disclosed rotating shields IMBT 100, 200, 300, achieving significantly anisotropic dose distributions, for all shield-radionuclide combinations evaluated. The disclosed rotating shields may maximize the amount of shielding material inside the tandem 20a since only single radionuclide-receiving passage is required.

Figure 9:
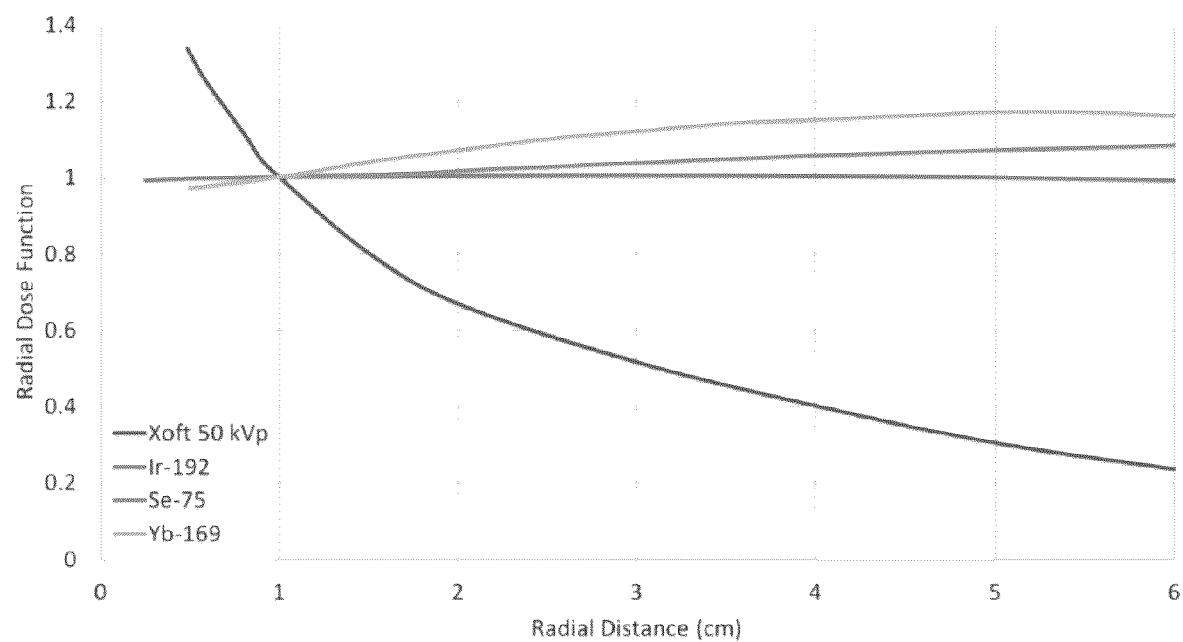
FIG. 9 is a graph showing radial dose in function of various brachytherapy sources normalized at 1 cm.
Figures 10A, 10B, 10C, 10D, 10E, 10F:
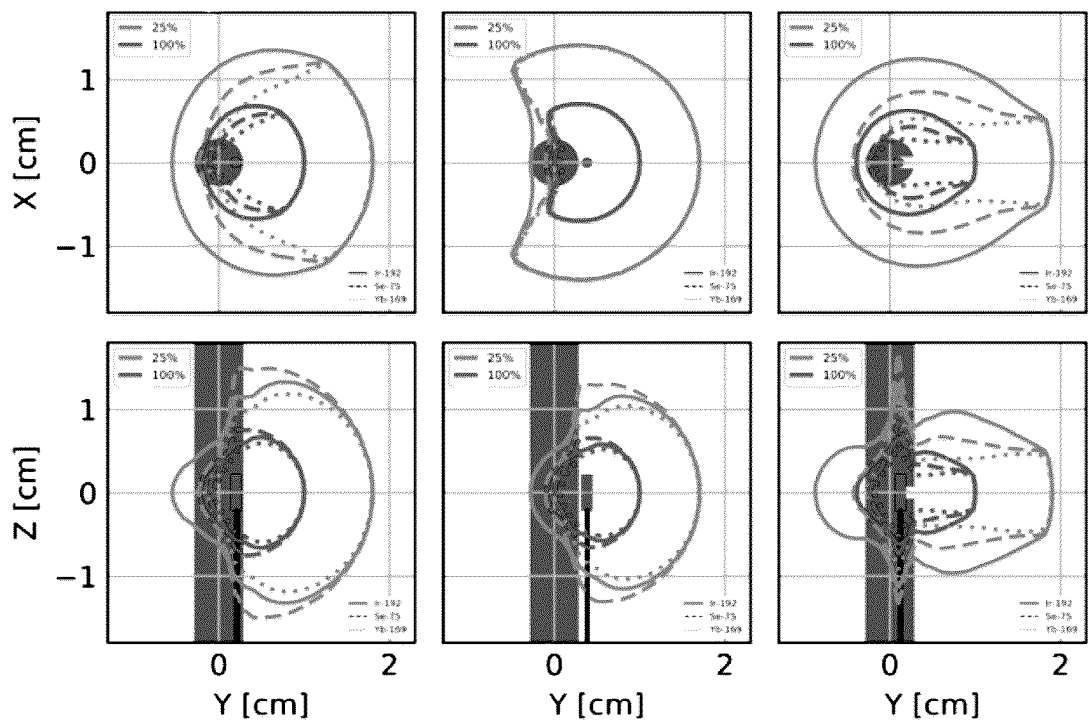
FIGS. 10a-10b are axial and longitudinal views of 100% and 25% isodose lines for the intracavitary shield of FIG. 3a made of platinum and with $^{192}$Ir (solid), $^{75}$Se (dashed) and $^{169}$Yb (dotted) radionuclides.
FIGS. 10c-10d are axial and longitudinal views of 100% and 25% isodose lines for the intracavitary shield of FIG. 2a made of platinum and with $^{192}$Ir (solid), $^{75}$Se (dashed) and $^{169}$Yb (dotted) radionuclides.
FIGS. 10e-10f are axial and longitudinal views of 100% and 25% isodose lines for the intracavitary shield of FIG. 4a made of platinum and with $^{192}$Ir (solid), $^{75}$Se (dashed) and $^{169}$Yb (dotted) radionuclides.

Although a very low energy beam is more easily shielded for IMBT, too low an energy may compromise the ability to treat patients with disease that has spread in the parametrium and paravaginal tissue. As shown in FIG. 9, it was observed that the radial dose decreases radially away from the central axis A when using a 50 kVp electronic BT source for treatment. By comparison, $^{76}$Se and $^{169}$Yb may be better alternative lower energy sources since their radial doses are substantially constant with an increasing radial distance from the central axis A.

The dose homogeneity, defined as $V_{200}\%/V_{100}\%$ was within 12% of the conventional tandem for all shield-radionuclide combinations. This may demonstrate that dose modulation may be achieved without introducing unacceptable hotspots in the patient when using the disclosed shields 100, 200, 300. The type-A shield 100 may be capable of reducing the dose on the shielded side of the tandem, at 1 cm, to 13.1%, 4.2% and 1.8% for $^{192}$Ir, $^{75}$Se and $^{169}$Yb, respectively.

As shown in FIGS. 8d to 8f, the type-A shield 100 may exhibit a relatively large beam width (~106°) in the azimuthal direction. This may limit its axial modulation capacity.

The type-B shield 200 having a single groove may improve upon the type-A shield 100 by filling the tandem with more attenuating material and simplifying the rotation mechanics as the shield rotation is concentric with the tandem. As shown in FIGS. 8g to 8i, a key improvement is the narrower azimuthal beam width (from 71 to 91 degrees depending of the radionuclide) without sacrificing transmission on the posterior end.

The type-C shield 300 may achieve small beam widths in the azimuthal and polar directions as depicted in FIGS. 8j to 8l. However, the resulting narrow beam may come at the expense of increasing posterior transmission. Indeed, since less shielding material is provided between the posterior side of the tandem and the radionuclide, less attenuation is achieved in this direction. A perusal of FIGS. 6g and 6j show that a greater dose is provided on the posterior side of the tandem.

A tightly collimated beam in the azimuthal and polar directions has the potential benefit of treating distance parametrial disease without significantly increasing dose to nearby OARs in the superior-inferior direction.

Retrospective Planning Study

A retrospective planning study was performed on a patient with locally advanced cervical cancer. The original treatment plan was treated using a hybrid intracavitary and interstitial needle implant with a conventional $^{192}$Ir brachytherapy source, which is current state-of-the-art treatment. Three IMBT plans were simulated and optimized; (1) Type-B shield with $^{192}$Ir, (2) Type-A shield with $^{169}$Yb and (3) Type-C shield with $^{169}$Yb. All IMBT plans were performed with shields composed of tungsten. IMBT plans only used source positions within the intracavitary applicator. Interstitial needles were not used in IMBT treatment plans to highlight the benefits of intracavitary-only IMBT. Each dwell position within the shielded intrauterine tandem were simulated using 16 angles (22.5 degrees between each IMBT dwell). Dwells within the vaginal (ring) portion of the intracavitary applicator were unshielded. A brachytherapy prescription dose of 27.5 Gy in 5 fractions was used in all treatment plans. To evaluate dose to tumor and OARs, dose was converted to 2 Gy equivalents (EQD2) and added to a pre-brachytherapy 45 Gy in 25 fraction whole pelvis external beam irradiation, consistent with standard-of-care protocol. Total EQD2 dose metrics for tumor and OARs were optimized according to the American Brachytherapy Society's recommendations: (1) D90%, the minimum dose to 90% of the tumor volume to receive approximately 80 Gy10 or more. (2) D2cc, the minimum dose to the most irradiated 2 cc of OAR to be less than 90 Gy3 for bladder and less than 75 Gy3 for rectum or sigmoid.

Referring to FIGS. 10a to 10f, normalized dose distributions at 1 cm from the center of the shielded applicator are shown for shields made of platinum. TFs are summarized in Table 3 and might be favorable for IMBT as TFs ranged between 4.1%-24.1% for $^{192}$Ir, 0.7%-8.6% for $^{75}$Se and 0.1-2.7% for $^{169}$Yb. On average, Pt shields attenuated 34% (19%-67%) more than W, for all source/shield combinations. Shields had a TF of at least 50% over an average arc of 245 degrees, 208 degrees and 283 degrees for $^{192}$Ir, $^{75}$Se and $^{169}$Yb, respectively.

In order to design a shield with a narrow emission window, the Type-C shields required the radionuclide-receiving passage to be placed closed to the applicator center, which increased the transmission relative to Type-B. Type-C shield did, however, exhibit a narrower beamlet when observed on longitudinal and axial planes.

TABLE 3

Transmission factors Dose [1 cm, 180 deg]/Dose[1 cm, 0 deg] for shield models made of tungsten (W) and platinum (Pt).

|  | Type-A | | Type-B | | Type-C | |
| --- | --- | --- | --- | --- | --- | --- |
|  | W | Pt | W | Pt | W | Pt |
| Ir-192 | 5.6% | 4.1% | 12.4% | 9.5% | 24.1% | 19.5% |
| Se-75 | 1.2% | 0.7% | 3.4% | 2.1% | 8.6% | 5.7% |
| Yb-169 | 0.3% | 0.1% | 0.1% | 0.8% | 2.7% | 1.6% |

Table 4 displays the clinical dose metrics for the conventional hybrid intracavitary/interstitial brachytherapy. A D90 of 80.2 $Gy_{10}$ for the tumor and D2cc to the bladder, rectum and sigmoid of 68.4 $Gy_3$, 59.0 $Gy_3$ and 59.5 $Gy_3$ were achieved for the clinical treatment plan. The dose metrics for the clinical treatment plan may be ideal in terms of tumor coverage and dose to OARs despite the locally advanced spread of the cancer.

TABLE 4

Total EQD2 doses for conventional $^{192}$Ir brachytherapy.

|  |  | Pre | Brachy | Total |  |
| --- | --- | --- | --- | --- | --- |
| TOTAL | Prescription | 44.3 | 35.5 | 79.8 |  |
| EQD2 | D90 | 44.3 | 35.9 | 80.2 |  |
| (Gy) | Bladder | 43.2 | 25.2 | 68.4 | <90 Gy |
|  | Rectum | 43.2 | 15.8 | 59.0 | <70-75 Gy |
|  | Sigmoid | 43.2 | 16.3 | 59.5 | <70-75 Gy |

Optimized IMBT dose distribution metrics are summarized in Tables 5, 6 and 7. IMBT with Type-B shield and $^{192}$Ir achieved a similar tumor and bladder dose to the conventional treatment plan. Rectum and sigmoid doses were approximately 10$Gy_3$ greater but are still below clinically acceptable dose constraints. IMBT with Type-B shield and $^{169}$Yb achieved a similar tumor and bladder dose to the conventional treatment plan. Compared to the $^{192}$Ir IMBT plan, the rectum and sigmoid received 7 Gy$_3$ less. The IMBT treatment plan using the Type-C shield and $^{169}$Yb delivered approximately 2 Gy$_{10}$ more to the tumor while respecting dose constraints as shown in Table 5.

TABLE 5

Total EQD2 doses for Type-A shield $^{192}$Ir IMBT

|  |  | Pre | Brachy | Total |  |
|---|---|---|---|---|---|
| TOTAL | Prescription | 44.3 | 35.5 | 79.8 |  |
| EQD2 | D90 | 44.3 | 32.9 | 77.2 |  |
| (Gy) | Bladder | 43.2 | 26.2 | 69.4 | <90 Gy |
|  | Rectum | 43.2 | 26.9 | 70.1 | <70-75 Gy |
|  | Sigmoid | 43.2 | 27.7 | 70.9 | <70-75 Gy |

TABLE 6

Total EQD2 doses for Type-A shield $^{169}$Yb IMBT

|  |  | Pre | Brachy | Total |  |
|---|---|---|---|---|---|
| TOTAL | Prescription | 44.3 | 35.5 | 79.8 |  |
| EQD2 | D90 | 44.3 | 32.9 | 77.2 |  |
| (Gy) | Bladder | 43.2 | 20.1 | 63.3 | <90 Gy |
|  | Rectum | 43.2 | 20.1 | 63.3 | <70-75 Gy |
|  | Sigmoid | 43.2 | 19.2 | 62.4 | <70-75 Gy |

TABLE 7

Total EQD2 doses for Type-C shield $^{169}$Yb IMBT

|  |  | Pre | Brachy | Total |  |
|---|---|---|---|---|---|
| TOTAL | Prescription | 44.3 | 35.5 | 79.8 |  |
| EQD2 | D90 | 44.3 | 37.6 | 81.9 |  |
| (Gy) | Bladder | 43.2 | 24.4 | 67.6 | <90 Gy |
|  | Rectum | 43.2 | 24.4 | 67.6 | <70-75 Gy |
|  | Sigmoid | 43.2 | 19.9 | 63.1 | <70-75 Gy |

Flexible Shields

Flexible/bendable metallic shields that can be placed inside applicators and rotated during the treatment with the shielded side toward the OARs and emission window towards the tumour are disclosed herein below. The metallic shields may be solid metal bars with cuts along its longitudinal axis enabling the metal bar to be flexible/bendable. The flexible shields disclosed herein below include shield sections that are secured to one another and that are pivotable one relative to the other while remaining attached to one another. Herein, "pivotable" implies that two consecutive section may become non-parallel one relative to the other such that a central axis of one of the two consecutive sections defines an angle with a central axis of the other of the two consecutive sections. The pivot motion is about an axis that may be normal to the central axis of the shield.

Referring to FIGS. 11a to 11d, a plurality of flexible shields 400, 500, 600, 700 are shown. The shield 400 has a slit pattern 400a on its outer surface that may enable it to be bent/flexed. The slit patterns 400a, 600a may be similar to a jigsaw puzzle (FIG. 11a and FIG. 11c). Alternatively, the slit patterns 500a, 700a may be a plurality of axially spaced apart slits being helicoid (FIG. 11b). Each slits is defined between two adjacent ones of shield sections 400b, 500b, 600b that are pivotable one relative to the other about an axis normal to the central axis A.

Referring now to FIGS. 12a-12b, another embodiment of a flexible shield is shown at 800. The shield 800 extends along a central axis A and defines a groove 800a for receiving the radionuclide seed. The shield 800 is a monolithic body 800e having flexible section 800f. The flexible section 800f includes a plurality of axially spaced apart slits 800b that extends from the outer surface 800g of the shield 800 toward a center thereof. Discs 800c are located between the slits 800b and are connected to one another via a core 800d of the shield 800. As a cross-sectional area of the core 800d is less than that of the discs 800c, the core 800d might allow the shield 800 to be bent. The spacing between the discs 800c allow for bending the core 800d.

Figures 13A, 13B:
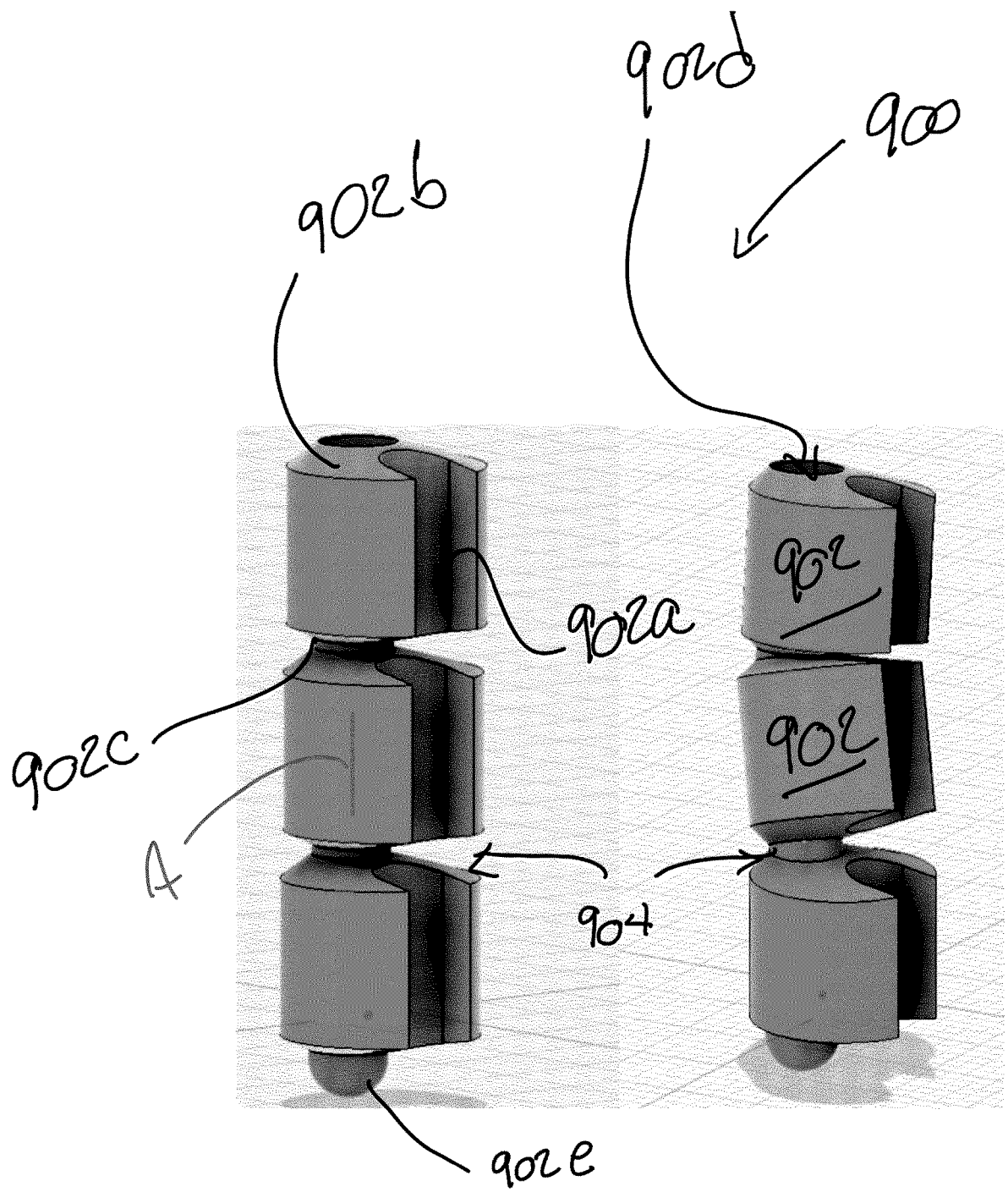
FIGS. 13a and 13b are schematic three dimensional views of a flexible intracavitary shield in accordance with another embodiment shown in two different positions.

Referring now to FIGS. 13a-13b, another embodiment of a flexible shield is shown at 900. The shield 900 includes a plurality of shield sections 902 that are interconnected to one another. Each of the shield sections 902 defines a groove 902a for receiving the radionuclide seed. The shield sections 902 defines two axial end faces, namely top axial end faces 902b and bottom axial end faces 902c. Rounded cavities 902d extend from the top axial end faces toward the bottom axial end faces and balls 902e extend from the bottom axial end faces and away from the top axial end faces. The balls 902e are received within the rounded cavities 902d. Articulations 904 are provided by a cooperation of the rounded cavities 902d and the balls 902e. The articulations 904, also referred to as flexible joints, allow the shield sections 902 to move one relative to the other to allow the shield 900 to bend.

In the embodiment shown, the axial end faces 902b, 902c slope toward one another away from the central axis A to avoid the top face of one sections 902 to abut against the bottom face of an adjacent section 902 before a suitable pivot angle between those two sections is achieved.

Figures 14A, 14B:
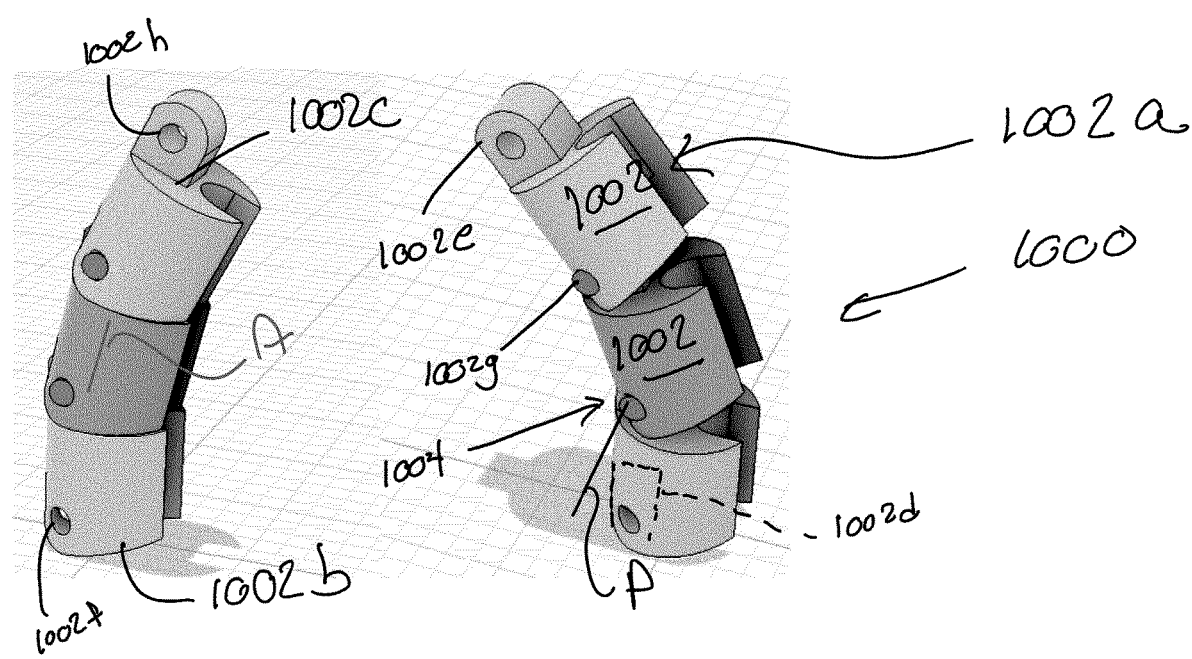
FIGS. 14a and 14b are schematic three dimensional views of a flexible intracavitary shield in accordance with another embodiment shown in two different positions.

Referring now to FIGS. 14a-14b, another embodiment of a flexible shield is shown at 1000. The shield 1000 includes a plurality of shield sections 1002 that are interconnected to one another. Each of the shield sections 1002 defines a groove 1002a for receiving the radionuclide seed. The shield sections 1002 defines two axial faces, namely bottom axial faces 1002b and top axial faces 1002c. Recesses 1002d extend from the bottom axial faces toward the top axial faces and tabs 1002e extend from the top axial faces and away from the bottom axial faces. The tabs 1002e are received within the recesses 1002d. Each of the shield sections 1002 defines an aperture 1002f for slidably receiving a pin 1002g therethrough. The apertures 1002f are in register with apertures 1002h through the tabs 1002e such that the pins 1002g extend through both of the apertures 1002f, 1002h. The pins 1002g lock the tabs into the recesses. Articulations 1004 are provided by a cooperation of the recesses 1002d, the tabs 1002e, and the pins 1002g. The pins 1002g define pivot axes P of two adjacent sections 1002 The articulations 1004, also referred to as flexible joints, allow the shield sections 1002 to move one relative to the other to allow the shield 1000 to bend.

Figures 15, 16:
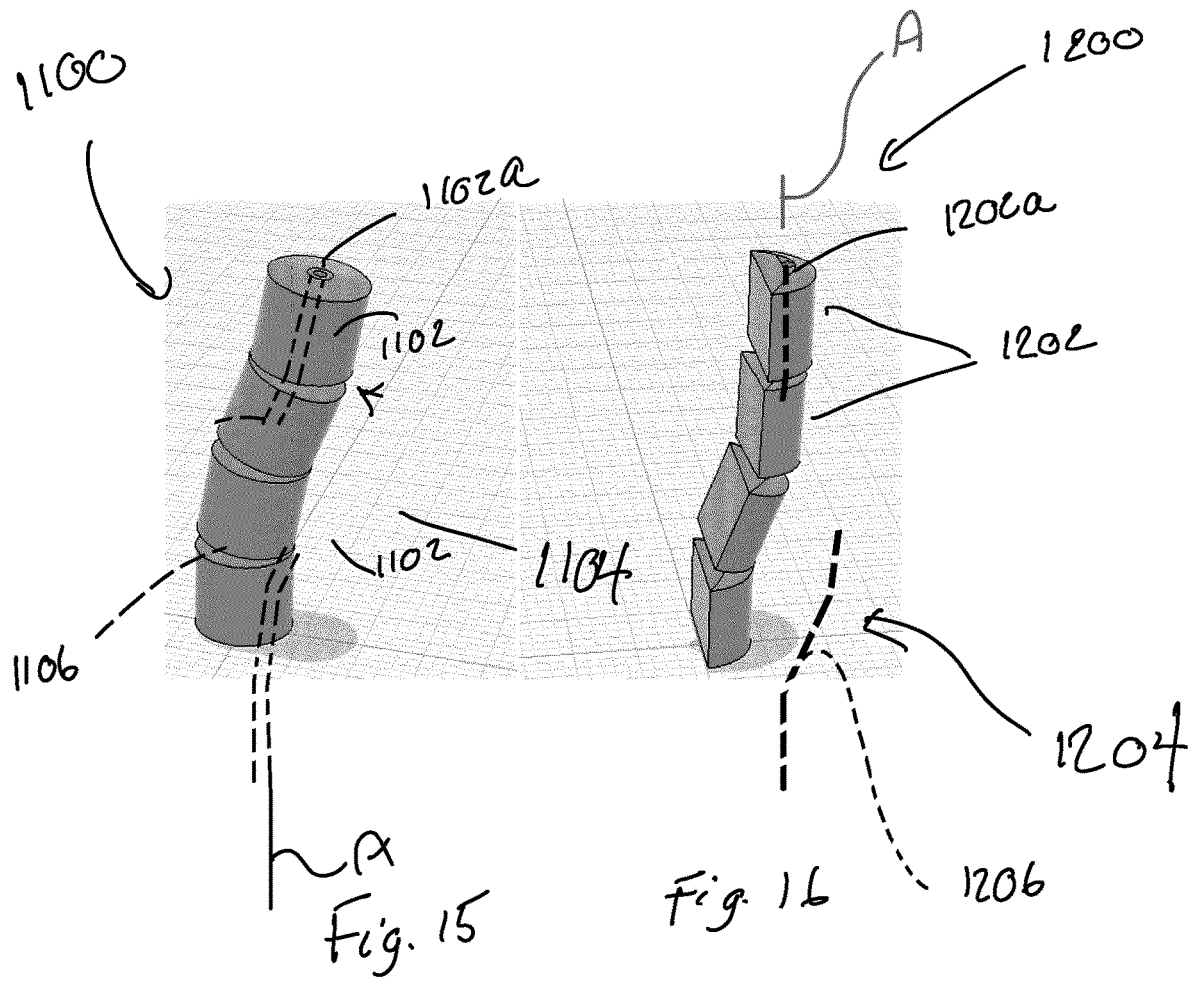
FIG. 15 is a schematic three dimensional view of a flexible intracavitary shield in accordance with another embodiment.
FIG. 16 is a schematic three dimensional view of a flexible intracavitary shield in accordance with another embodiment.

Referring now to FIG. 15, another embodiment of a flexible shield is shown at 1100. The shield 1100 includes a plurality of interconnected shield sections 1102 each having a central aperture 1102a in register with one another. Each sections is cylindrically shaped. Flexible joints 1104 are defined using any suitable means to allow the shield sections 1102 to move one relative to the others. In the embodiment shown, a flexible rod 1106 extends through the apertures 1102a to connect the sections 1102 with one another and to allow each sections 1102 to pivot relative to its neighbouring sections 1102. In the embodiment shown, the radionuclide-receiving passage and the flexible rod 1106 are concentric. The rod 1106 may be annular. The axial end faces of each sections 1102 are tapered to allow a pivot motion between each two adjacent ones of the sections 1102.

Referring now to FIG. 16, another embodiment of a flexible shield is shown at 1200. The shield 120 includes a plurality of interconnected shield sections 1202 each having an aperture 1202*a*. Each sections 1202 is an half-cylinder. Flexible joints 1204 are defined using any suitable means to allow the shield sections 1202 to move one relative to the others. In the embodiment shown, a flexible rod 1206 extends through the apertures 1202*a* to connect the sections 1202 with one another and to allow each sections 1202 to pivot relative to its neighbouring sections 1202. The axial end faces of each sections 1202 are tapered to allow a pivot motion between each two adjacent ones of the sections 1202.

Figures 17A, 17B:
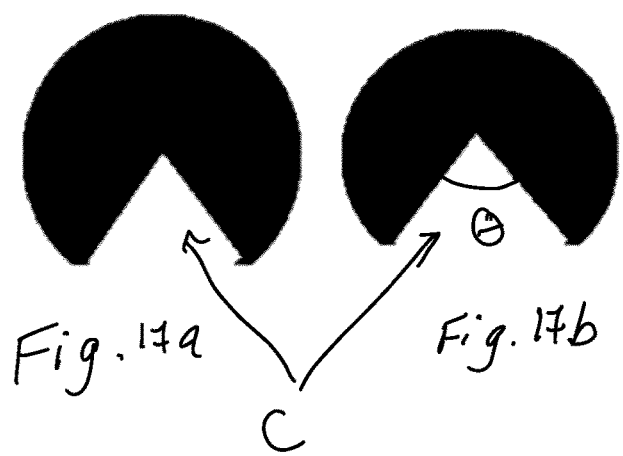
FIGS. 17a and 17b are cross-sectional views of flexible intracavitary shields in accordance with yet other embodiments.

Referring now to FIGS. 17*a* and 17*b*, example of possible cross-sections of the shield sections 1102 and 1202 of the shields 1100, 1200 are shown. Radionuclide-receiving passages C are defined by concave portions of the sections. An angle θ may be varied from 0 degree as shown in FIG. 15 to 180 degrees as shown in FIG. 16 and of about 45 to 90 degrees as shown in FIGS. 17*a*, 17*b*.

In the present disclosure, the expression "about" means that a value may vary by plus or minus 10% of its value. For instance, a value of about 10 means that the value may range from 9 to 11. It will be appreciated that the dimensions disclosed herein are adjustable to cater to different applications. For instance, 1 to 3 mm may be added to the thickness of the shields, length can be chosen to cover the entire tandem for the applicator model used. For some dimensions, their value may be varied by plus or minus 1 to 2 mm.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A shield assembly for an intensity modulated brachytherapy (IMBT) system, comprising:
   a tubular applicator engageable to a rotating mechanism of the IMBT system, the tubular applicator having a peripheral wall enclosing an internal cavity extending longitudinally along a central axis;
   a radiation shield extending axially along the central axis and received within the internal cavity, the radiation shield made of an MRI-compatible and radiation attenuating material, the radiation shield including radiation shield sections interconnected to one another and pivotable one relative to the other about axes transverse to the central axis, the radiation shield sections are interconnected to one another by joints, the joints permitting rotation about the axes and preventing the radiation shield sections from translating one relative to the other along the central axis, a joint of the joints including:
      a ball protruding axially from an axial end face of one of the radiation shield sections and a rounded cavity extending from an axial end face of an adjacent one of the radiation shield sections, the ball received within the rounded cavity, or
      a tab protruding from an axial end face of one of the radiation shield sections and a recess extending from the axial end face of an adjacent one of the radiation shield sections, the tab pivotably received within the recess, the tab locked within the recess via a pin extending through a first aperture defined through the tab and through a second aperture defined through the adjacent one of the radiation shield sections; and
   a radionuclide-receiving passage within the internal cavity of the tubular applicator, the radionuclide-receiving passage extending axially and being radially offset from the central axis.

2. The shield assembly of claim 1, wherein the central axis is free of intersection with the radionuclide-receiving passage.

3. The shield assembly of claim 1, wherein the radionuclide-receiving passage is a groove defined by the radiation shield and extending axially along the central axis, the groove extending radially from an outer face of the radiation shield toward the central axis.

4. The shield assembly of claim 1, wherein the radionuclide-receiving passage is defined between a cylindrical outer face of the radiation shield and the peripheral wall.

5. The shield assembly of claim 1, wherein the radionuclide-receiving passage is a bore extending through the radiation shield.

6. The shield assembly of claim 5, wherein the radiation shield defines apertures extending from an outer surface of the radiation shield to the bore, the apertures axially spaced-apart from one another along the central axis and being circumferentially aligned with one another.

7. The shield assembly of claim 5, wherein a ratio of a distance (D3) between a center of the bore and a center of the radiation shield to an internal diameter (D8) of the tubular applicator ranges from 0.06 to 0.2.

8. The shield assembly of claim 7, wherein a ratio of a diameter (D7) of the bore to a the internal diameter (D8) of the tubular applicator ranges from 0.09 to 0.3, wherein a ratio of a distance (d3) taken along the central axis between two adjacent ones of the apertures to the internal diameter of the tubular applicator ranges from 0.6 to 2, and wherein a ratio of a diameter (D4) of the apertures to the internal diameter (D8) of the tubular applicator ranges from 0.06 to 0.2.

9. An intensity modulated brachytherapy (IMBT) system, comprising a rotating system and a shield assembly drivingly engaged to the rotating system for rotating the shield assembly about a central axis thereof, the shield assembly having: a tubular applicator including a peripheral wall enclosing an internal cavity extending axially along the central axis; a radiation shield within the internal cavity and extending axially along the central axis, the radiation shield made of an MRI-compatible and radiation attenuating material; and a radionuclide-receiving passage within the internal cavity of the tubular applicator, the radionuclide-receiving passage being eccentric relative to the internal cavity of the tubular applicator, the radiation shield defining apertures extending from an outer surface of the radiation shield to the radionuclide-receiving passage, the apertures axially spaced-apart from one another along the central axis and being circumferentially aligned with one another, the apertures located at a single circumferential position relative to the central axis, the radiation shield devoid of apertures outside the single circumferential position, wherein the radiation shield includes: radiation shield sections interconnected to one another and pivotable one relative to the other about an axis normal to the central axis; and a monolithic body defining a flexible section, the flexible section including a plurality of slits, each of the slits extending from an outer face of the monolithic body toward the central axis, the slits ending at a core, discs defined between the slits and being axially spaced apart from one another to allow bending of the core.

10. The IMBT system of claim 9, wherein the peripheral wall defines a slit pattern.

11. The IMBT system of claim 10, wherein slits of the slit pattern have a jigsaw shape or a helicoid shape.

12. The IMBT system of claim 9, wherein the radiation shield sections are interconnected to one another by a joint.

13. The IMBT system of claim 12, wherein the joint includes a ball protruding axially from an axial end face of one of the radiation shield sections and a rounded cavity extending from an axial end face of an adjacent one of the radiation shield sections, the ball received within the rounded cavity.

14. The IMBT system of claim 12, wherein the joint includes a tab protruding from an axial end face of one of the radiation shield sections and a recess extending from the axial end face of an adjacent one of the radiation shield sections, the tab pivotably received within the recess, the tab locked within the recess via a pin extending through a first aperture defined through the tab and through a second aperture defined through the adjacent one of the radiation shield sections.

15. The IMBT system of claim 9, wherein the radiation shield sections are connected to one another via flexible rods extending through registering apertures defined by the radiation shield sections.

16. A shield assembly for an intensity modulated brachytherapy (IMBT) system, comprising:

a tubular applicator engageable to a rotating mechanism of the IMBT system, the tubular applicator having a peripheral wall enclosing an internal cavity extending longitudinally along a central axis;

a radiation shield extending axially along the central axis and received within the internal cavity, the radiation shield made of an MRI-compatible and radiation attenuating material, the radiation shield including shield sections interconnected to one another via a core, the core being flexible, the shield sections pivotable one relative to the other about axes transverse to the central axis via flexion of the core; and a radionuclide-receiving passage within the internal cavity of the tubular applicator, the radionuclide-receiving passage extending axially and being radially offset from the central axis.

17. The shield assembly of claim 16, wherein the core and the shield sections are parts of a monolithic body of the radiation shield, the shield sections interspaced between slits, each of the slits extending from an outer face of the monolithic body toward the central axis, the slits ending at the core, the shield sections being discs defined between the slits and being axially spaced apart from one another to allow bending of the core.

18. The shield assembly of claim 16, wherein the core is defined by a flexible rod extending through registering apertures defined by the shield sections.

* * * * *